US012307206B2

(12) United States Patent
Sontag et al.

(10) Patent No.: US 12,307,206 B2
(45) Date of Patent: May 20, 2025

(54) CLINICAL DOCUMENTATION SYSTEM

(71) Applicants: Massachusetts Institute of Technology, Cambridge, MA (US); Beth Israel Deaconess Medical Center, Inc., Boston, MA (US)

(72) Inventors: David Sontag, Brookline, MA (US); Luke Scott Murray, Brooklyn, NY (US); Divya Gopinath, Millwood, NY (US); Monica Nayan Agrawal, Boston, MA (US); David R. Karger, Cambridge, MA (US); Steven Horng, Boston, MA (US)

(73) Assignees: Massachusetts Institute of Technology, Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 241 days.

(21) Appl. No.: 17/940,170

(22) Filed: Sep. 8, 2022

(65) Prior Publication Data
US 2023/0071217 A1 Mar. 9, 2023

Related U.S. Application Data

(60) Provisional application No. 63/241,760, filed on Sep. 8, 2021.

(51) Int. Cl.
*G06F 40/205* (2020.01)
*G06F 40/10* (2020.01)
(Continued)

(52) U.S. Cl.
CPC .............. *G06F 40/30* (2020.01); *G06F 40/10* (2020.01); *G06F 40/205* (2020.01); *G16H 10/60* (2018.01)

(58) Field of Classification Search
CPC .......... G06F 40/40; G06F 40/30; G06F 40/10; G06F 40/205; G16H 40/20; G16H 40/67;
(Continued)

(56) References Cited

U.S. PATENT DOCUMENTS 10,546,653 B2 * 1/2020 Zasowski ............... G16H 50/20
11,309,079 B2 * 4/2022 Radhakrishnan ...... G16H 40/67
(Continued)

OTHER PUBLICATIONS

Divya Gopinath et al., "Fast, Structured Clinical Documentation via Contextual Autocomplete," Proceedings of Machine Learning Research, 106:1-25 (2020).
(Continued)

*Primary Examiner* — Vijay B Chawan
(74) *Attorney, Agent, or Firm* — Occhiuti & Rohlicek LLP

(57) ABSTRACT

A computer implemented method for managing medical information includes displaying a number of user interface elements within a graphical user interface, receiving medical information for a patient in a first user interface element of the user interface elements, processing the medical information to identify one or more semantic items, the one or more semantic items including a first semantic item, processing a medical record for the patient according to first semantic item, the processing including identifying a number of medical information items related to the first semantic item, and presenting at least some medical information items of the number of medical information items in a second user interface element configured to display medical information items related to the first semantic item.

24 Claims, 23 Drawing Sheets

(51) Int. Cl.
*G06F 40/30* (2020.01)
*G16H 10/60* (2018.01)

(58) Field of Classification Search
CPC ........ G16H 10/60; G16H 50/70; G16H 50/20; G16H 30/20; G16H 10/20; G16H 50/30
USPC .............................................................. 704/9
See application file for complete search history.

(56) References Cited

U.S. PATENT DOCUMENTS

| | | | | |
|---|---|---|---|---|
| 11,520,847 | B2* | 12/2022 | Weber | G06F 16/358 |
| 11,636,926 | B1* | 4/2023 | Emery | G16H 40/20 |
| | | | | 705/3 |
| 12,020,814 | B1* | 6/2024 | McNair | G16H 50/70 |
| 2012/0197657 | A1* | 8/2012 | Prodanovic | G16H 40/20 |
| | | | | 705/2 |
| 2013/0308839 | A1* | 11/2013 | Taylor | G16H 30/20 |
| | | | | 382/128 |
| 2015/0019260 | A1* | 1/2015 | Samani | G16H 10/60 |
| | | | | 705/3 |
| 2016/0012187 | A1* | 1/2016 | Zasowski | G16H 40/67 |
| | | | | 705/3 |
| 2017/0199963 | A1* | 7/2017 | Kondadadi | G16H 15/00 |
| 2019/0156921 | A1* | 5/2019 | Kohli | G06F 16/93 |
| 2020/0381092 | A1* | 12/2020 | Granvold | G16H 40/67 |
| 2021/0090694 | A1* | 3/2021 | Colley | G16H 15/00 |
| 2021/0407632 | A1* | 12/2021 | Carlson | G16H 40/63 |
| 2022/0148689 | A1* | 5/2022 | Gill | G16H 10/60 |
| 2023/0260665 | A1* | 8/2023 | Swisher | G16H 50/70 |
| | | | | 705/2 |

OTHER PUBLICATIONS

Luke Murray et al., MedKnowts: UNified Documentation and Information Retrieval for Electronic Health Records, In UIST 2021: ACM Symposium on User Interface Software and Technology, Oct. 10-31, 2021 (15 pages).

Anonymous, "Electronic Health Record—Wikipedia," Sep. 3, 2021, pp. 1-25 retrieved from the internet (Nov. 28, 2022): https://en.wikipedia.org/w/index.php?title=Electronic_health_record&oldid=1042176261.

International Search Report, PCT Application No. PCT/US2022/042837, mailed Dec. 13, 2022 (5 pages).

* cited by examiner hypertension no hx of alcoholism
glucose
tylenol
chest pain no hx of chest pain
hysterectomy
systolic blood pressure 423 — hypertension
425 — glucose
427 — tylenol
429 — chest pain
431 — hysterectomy
433 — systolic blood pressure

FIG. 4

Patient has a history of htn and afib on coumadin. She is concerned about possible prediabetes — A1c 5.20 (2/19/2020), glucose 121 normal. She presents with fever and wheezing but no chills. o2sat 95 slightly low. Patient had oophorectomy last year.

SNOMED CT — 635
First Data Bank — 637
SNOMED CT — 635
SNOMED CT — 635
N/A
LOINC — 639

Constitutional: No fever, no chills
Head / Eyes: No diplopia
ENT: no earache
Resp: No cough
Cards: No chest pain
Abd: No abdominal pain
Flank: No dysuria
Skin: No rash
Ext: No back pain
Neuro: No headache
Psych: No depression

CLINICAL DOCUMENTATION SYSTEM

CROSS-REFERENCES TO RELATED APPLICATIONS

This application claims the benefit of U.S. Provisional Application No. 63/241,760 filed Sep. 8, 2021, the entire contents of which are incorporated herein.

BACKGROUND OF THE INVENTION

This invention relates to a clinical documentation system.

Complete and well-written clinical documentation provides cogent clinical narratives, which help clinicians understand a patient's case, function as a communication method between clinicians, and serve as learning tools for improving future practices. In an effort to improve clinical documentation practices, Electronic Health Records (EHRs) were adopted by the medical community. EHR platforms promised to improve quality of care, save time, support collaboration and data sharing, and prevent clinical errors. But a side effect of using EHR platforms is that clinicians often spend more time navigating EHRs than physically communicating with patients. EHR usage is a leading cause of physician burnout and stress. The documentation process can be tedious, time-consuming, and error-prone because clinicians are faced with multi-faceted requirements and fragmented interfaces for information exploration and documentation.

The challenges described above exist across both inpatient and outpatient hospital settings (e.g., in primary care and oncology settings) and are exacerbated in the Emergency Department, where clinicians often see 35 patients in one shift, during which they synthesize an often previously unknown patient's medical record to reach a tailored diagnosis and treatment plan.

SUMMARY OF THE INVENTION

Aspects described herein support information synthesis in a clinical documentation setting by enabling rapid contextual access to the patient's medical record. Aspects include an integrated note-taking editor and information retrieval system that unifies the clinical documentation and search process and provides concise synthesized concept-oriented slices of a patient's medical record. Aspects automatically capture structured data while still allowing users the flexibility of documenting a patient's medical record using natural language. The structured data is leveraged to enable easier parsing of long notes, auto-population of text, and proactive information retrieval from sources including the patient's medical record, easing the documentation burden.

In a general aspect, a computer implemented method for managing medical information includes displaying a number of user interface elements within a graphical user interface, receiving medical information for a patient in a first user interface element of the user interface elements, processing the medical information to identify one or more semantic items, the one or more semantic items including a first semantic item, processing a medical record for the patient according to first semantic item, the processing including identifying a number of medical information items related to the first semantic item, and presenting at least some medical information items of the number of medical information items in a second user interface element configured to display medical information items related to the first semantic item.

Aspects may include one or more of the following features.

The method may include parsing an electronic health record for the patient to identify the medical information items. The medical input may include textual input. Receiving the medical input may include processing the textual input as it is entered to present one or more predicted semantic items associated with the textual input. The method may include determining the one or more predicted semantic items associated with the textual input according one or more medical ontologies and/or medical terminology databases. Processing the medical information to identify one or more semantic items may include processing the textual input to identify words or phrases associated with semantic items.

The method may include parsing an electronic health record for the patient to identify at least some of the one or more semantic items. The presenting of the at least some medical information items of the number of medical information items in the second user interface element may occurs when a user interacts with the first semantic item. Presenting the at least some medical information items of the number of medical information items in the second user interface element may include causing the second user interface element to be displayed.

The method may include presenting the one or more semantic items in the first user interface element. Presenting the semantic items may include color coding the semantic items according to contexts associated with the semantic items. Each context associated with semantic items may be selected from a group including a condition context, a lab result context, a medication context, a symptom context, a procedure context, and a vitals context.

Each semantic item may be associated with a context selected from a group including a condition context, a lab result context, a medication context, a symptom context, a procedure context, and a vitals context. The method may include populating a third user interface element at least some of the one or more semantic items. The method may include detecting that at least some of the medical information associated with a number of semantic items and displaying an indicator associated with the at least some medical information in the first user interface element based on the detecting. The method may include presenting a menu for disambiguating the medical information by selecting a semantic item from the number of semantic items.

The first user interface element and the second user interface element may be displayed simultaneously. The method may include identifying at least some semantic items of the one or more semantic items as negated semantic items and presenting a negation indicator along with the identified semantic items.

In another general aspect, a system for managing medical information includes a display for displaying a number of user interface elements within a graphical user interface, an input for receiving medical information for a patient in a first user interface element of the number of user interface elements, and one or more processors configured to process the medical information to identify one or more semantic items, the one or more semantic items including a first semantic item, process a medical record for the patient according to first semantic item, the processing including identifying a number of medical information items related to the first semantic item, and cause presentation, using the display, of at least some medical information items of the number of medical information items in a second user interface element configured to display medical information items related to the first semantic item.

In another general aspect, software embodied on a non-transitory, computer readable medium includes instructions for implementing a method for managing medical information, where the method includes displaying a number of user interface elements within a graphical user interface, receiving medical information for a patient in a first user interface element of the number of user interface elements, processing the medical information to identify one or more semantic items, the one or more semantic items including a first semantic item, processing a medical record for the patient according to first semantic item, the processing including identifying a number of medical information items related to the first semantic item, and presenting at least some medical information items of the number of medical information items in a second user interface element configured to display medical information items related to the first semantic item.

Aspects may have one or more of the following advantages.

Aspects described herein advantageously address problems that arise from view fragmentation in EHR platforms. View fragmentation exists in conventional EHR platforms during both information retrieval and data exploration over a patient's medical history and information entry. Because structured and unstructured data can be difficult to reconcile, conventional EHR platforms often store and display information in separate pages or windows, and physicians have to synthesize a narrative for the patient by navigating across a variety of sources. This creates increased cognitive burden to discover unstructured information, and studies have shown that clinicians spend more time reading past notes than doing any other activity in EHRs. Further, fragmented interfaces hinder comprehensibility and necessitate frequent task switching. To avoid this task switching, some clinicians have developed coping mechanisms such as copying from previous notes or using autofill techniques for naive pre-population of text. Indiscriminate use of such auxiliary functions can cause documentation to become bloated, making it difficult for clinicians to parse important clinical information, and potentially even propagating errors. Aspects described herein alleviate view fragmentation in clinical documentation systems by automatically identifying and presenting relevant contextual information to clinicians as they access and modify an EHR.

Aspects described herein advantageously provide clinicians with access to a curated subset of the medical record, displayed as a collection of concept-oriented cards. Each card provides a succinct display of high value information curated for a single clinical concept. The card relevant to the most recently recognized term is automatically displayed next to the note in a preview pane, providing a passive stream of relevant information to the clinician. Cards can also be manually pinned to the sidebar where they can be seen by all users working on the note. Pinned cards act as a persistent and shared collection of data which is particularly pertinent to a given patient's context.

Aspects described herein advantageously provide a contextual autocomplete functionality which saves documentation time. Advantageously, the autocomplete does not require a trigger character—so it does not disrupt the prior documentation workflow—and displays options for structured data entry (e.g., lab values) as the user types, removing the need to memorize content importing phrases. When autocomplete is not used, aspects employ keyword matching, referred to as post-recognitions, to automatically identify clinical terms as the clinician types. Both auto-completed and post-recognized terms are transformed into structured interactive elements, sometimes referred to as "semantic items" or "chips." This structure enables live semantic highlighting that enables easier parsing of long notes and automatic population of repetitive text fields, easing documentation burden. Both contextual autocomplete and post-recognitions may use a machine learning based system for prediction of what concepts are likely to be documented (in the case of contextual autocomplete) or have been documented (in the case of post-recognition).

Aspects also advantageously use structured data to automatically display information cards in an attached preview pane as the user types. Proactively displayed cards provide concise summaries of relevant medical history, reducing the context-switching required to synthesize a note. Each card is a concept-oriented view such that information is grouped by underlying concept (e.g., the labs, medications, and notes related to a condition) rather than by data modality (all medications at once). In addition to the automatically surfaced cards, semantic items embedded in the note and in cards serve as links to related cards, providing direct access to the relevant medical history from the note context and other cards. Cards can be surfaced in-line by hovering on a semantic item or in the preview pane by clicking on a semantic item. This provides an additional avenue for contextual information retrieval without dividing attention between views. Finally, cards can be pinned to an attached sidebar, which persists the card to a view shared by the clinical care team, allowing for easier bookmarking, collaboration, and data sharing without directly copying to contribute to note bloat.

Other features and advantages of the invention are apparent from the following description, and from the claims.

BRIEF DESCRIPTION OF THE DRAWINGS

FIG. 4 shows different types of semantic items.

FIG. 6 shows ontologies and databases associated with classes of semantic items.

FIG. 7 shows an autocomplete functionality with a drop-down menu.

FIG. 11 shows a modifier functionality and indicator.

FIG. 12 shows default text population of one field using sematic items from another field.

FIG. 13 shows a second example of default text population of one field using sematic items from another field.

FIG. 15 shows an example of an informational card.

FIG. 16 shows an informational card displayed during text entry.

FIG. 17 shows an informational card displayed by clicking a semantic item.

FIG. 18 shows an informational card being displayed inline.

DETAILED DESCRIPTION

1 System Overview

Figure 1:
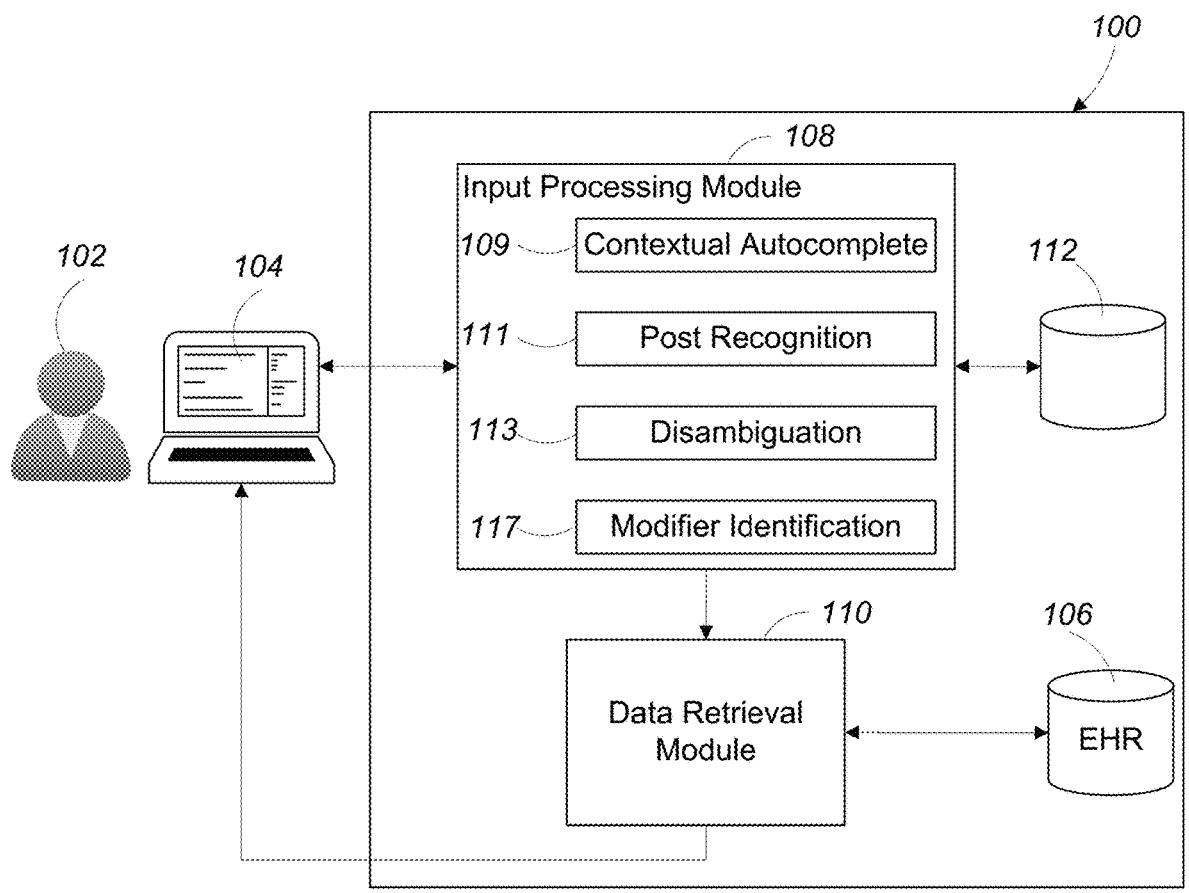
FIG. 1 is a schematic diagram of a clinical documentation system.

Referring to FIG. 1, a clinical documentation system 100 is configured to assist a user 102 (e.g., a clinician including a doctor, nurse, or scribe) in diagnosing, treating, and documenting a medical condition of a patient. Very generally, as the user 102 interacts with the system 100 through a graphical user interface 104, the system 100 accesses the patient's electronic health record (EHR) 106 and one more medical terminology databases 112 to both assist data entry by the user 102 and provide timely, clinically pertinent information to the user 102 via the graphical user interface 104.

In some examples, the clinical documentation system 100 includes an input processing module 108 and a data retrieval module 110. The input processing module 108 processes textual input using a medical terminology database 112 to identify semantic items (e.g., semantically interesting or important words or phrases) in the input. In some examples, the input processing module 108 includes a number of sub-modules including a contextual autocomplete module 109, a post-recognition module 111, a disambiguation module 113, and a modifier identification module 117. The input processing module 108 and its sub-modules work in tandem with the graphical user interface 104 to assist the user in entering the semantic items, as is described in greater detail below. In some examples, the identified semantic items are highlighted in the graphical user interface 104.

Semantic items identified by the input processing module 108 are provided to the data retrieval module 110, which uses those items to access additional, clinically pertinent information (e.g., lab values, medications, or test results) from the patient's electronic health record 106. The data retrieval module 110 provides the additional information to the graphical user interface 104, where it is displayed to the user 102 in a useful format (e.g., graphs, pre-formatted information "cards," or dropdown menus), as is described in greater detail below.

2 User Interface

Figure 2:
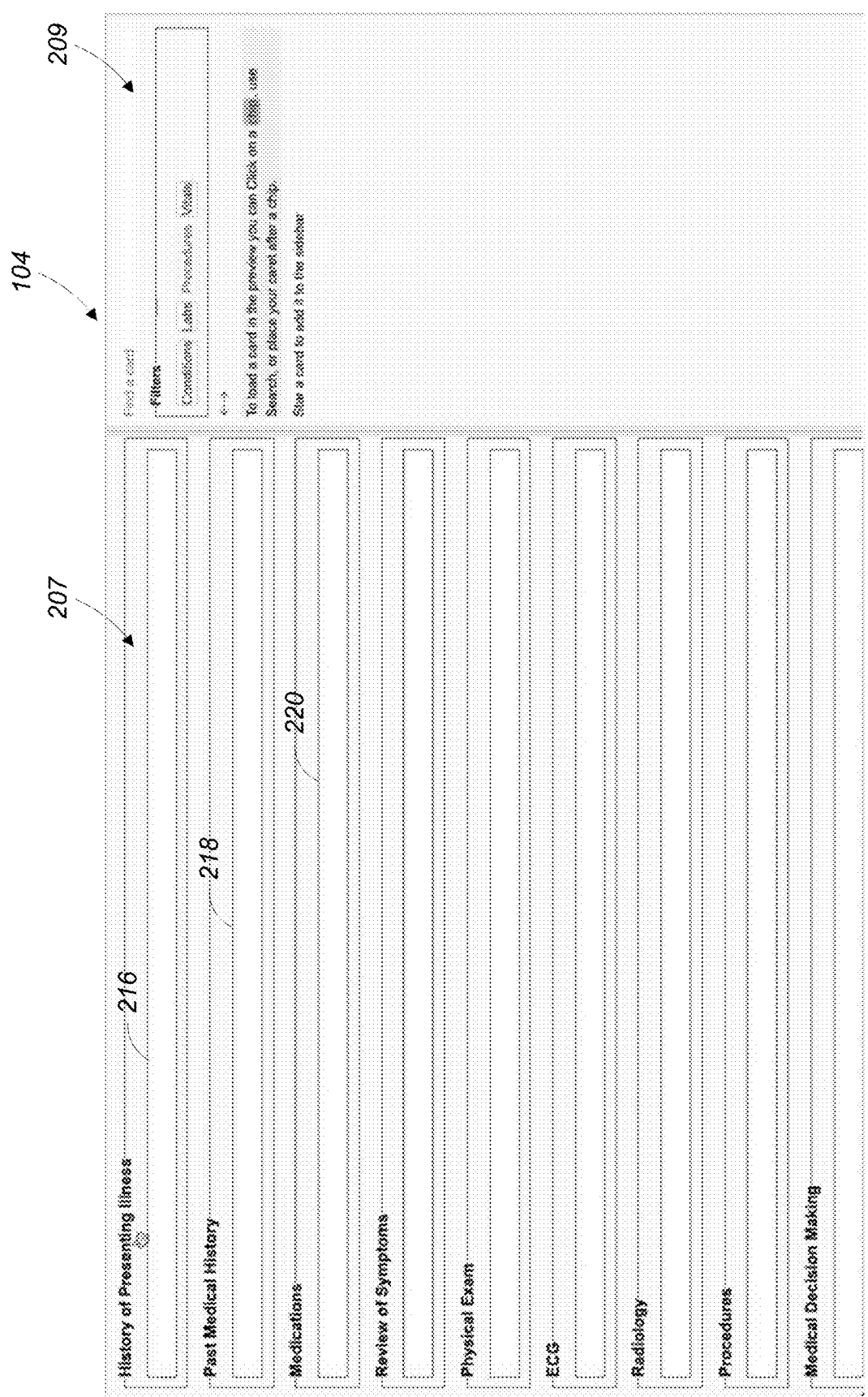
FIG. 2 is a graphical user interface.

Referring to FIG. 2, one example of the user interface 104 includes a clinical note 207 and a sidebar 209. The clinical note 207 includes several fields including "History of Presenting Illness" field 216, a "Past Medical History" field 218 and a "Medications" field 220, among others. The user 102 (e.g., a medical practitioner) completes some or all of the fields over the course of treating a patient (e.g., during a patient visit). As is described in greater detail below, the sidebar 209 is used to present pertinent additional information to the user 102 as they interact with the clinical note 207.

2.1 Clinical Note

2.1.1 Automatic Population from Medical Record

Figure 3:
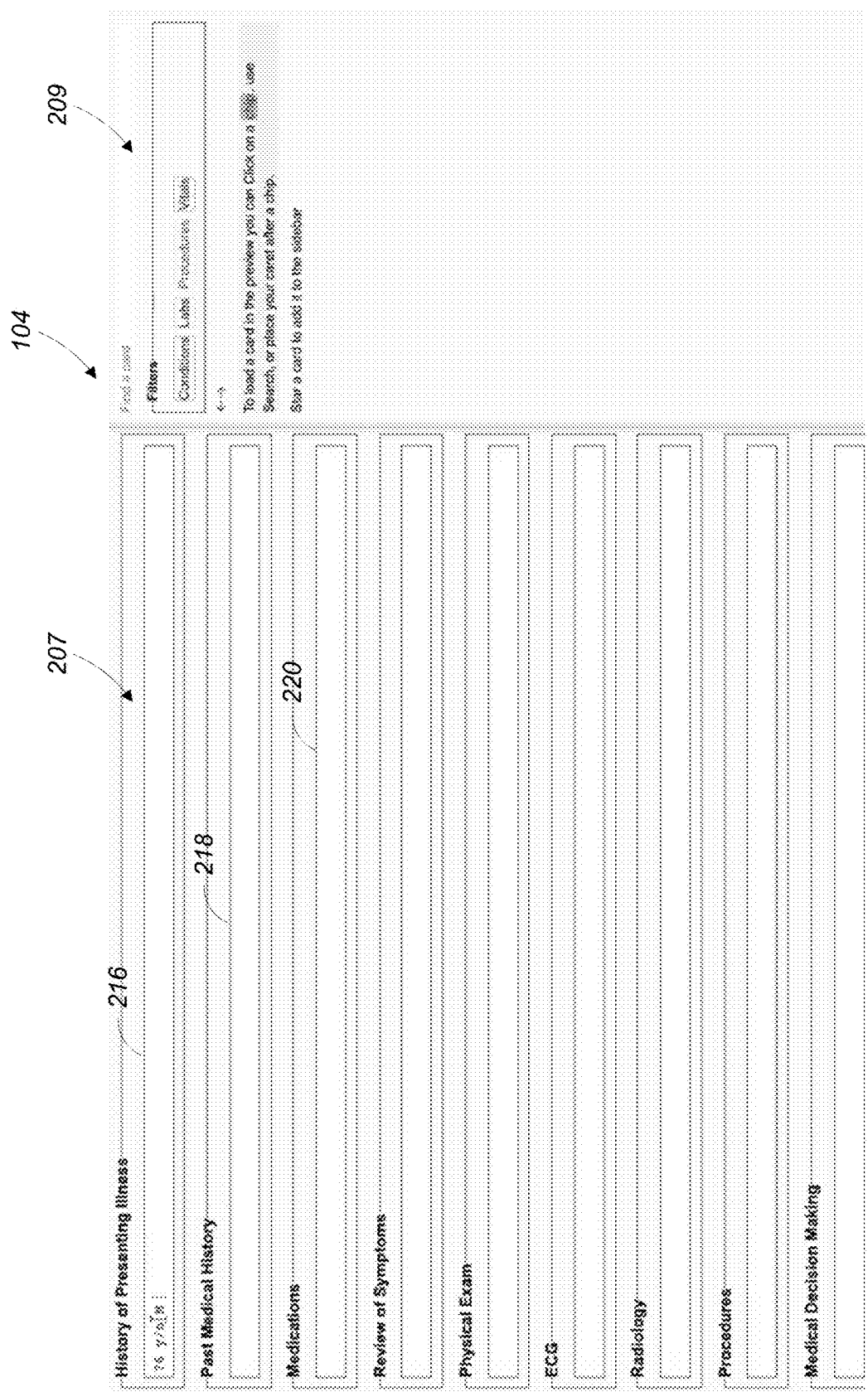
FIG. 3 shows automatic population of a field from an EHR.

Referring to FIG. 3, in some examples, the clinical documentation system 100 automatically populates parts of the user interface 104 using information already present in a patient's electronic health record. For example, when the user 102 interacts with a field of the clinical note 207 (e.g., by "clicking" in the field), the input processing module 108 causes the data retrieval module 110 to retrieve relevant information associated with the field. The retrieved information is provided to the user interface 104, where it is displayed in the field of the clinical note 207 that was interacted with.

For example, in FIG. 3, the user 102 has previously clicked their mouse cursor in the "History of Presenting Illness" field 216. The "click" input is provided to the input processing module 108, which determines that the user 102 has clicked in the empty "History of Presenting Illness" field 216. The input processing module 108 instructs the data retrieval module 110 to access the patient's EHR 106 for pre-populating the "History of Presenting Illness" field 216. The data retrieval module 110 accesses the patient's EHR 106 and discovers that the patient is a 76-year-old male (represented as "76 y/o M"). That information is provided to the graphical user interface 104, which pre-populates the "History of Presenting Illness" field 216 with "76 y/o M."

In some examples, different fields are configured with rules or templates to determine what data is retrieved from the EHR 106 and pre-populated in the fields. For example, a rule or template associated with the "History of Presenting Illness" field 216 is based on the knowledge that users 102 often begin their narrative in the field by referencing the patient's medical record to determine and enter the patient's age and sex. The auto-population rule obviates the need for the user 102 to switch back and forth between the clinical note 207 and the patient's EHR 106 to determine that information.

Similarly, the other fields in the clinical note 207 may be associated with different pre-population rules or templates, as is illustrated in later figures.

2.1.2 Semantic Items

As the user 102 continues entering text into the fields of the user interface 104, the input processing module 108 also processes the entered text to identify and highlight semantic items. In general, the semantic items are interactive, structured elements which provide information scent about recognized vocabulary, semantic highlighting, access to inline documentation, and contextual information retrieval.

Figure 5:
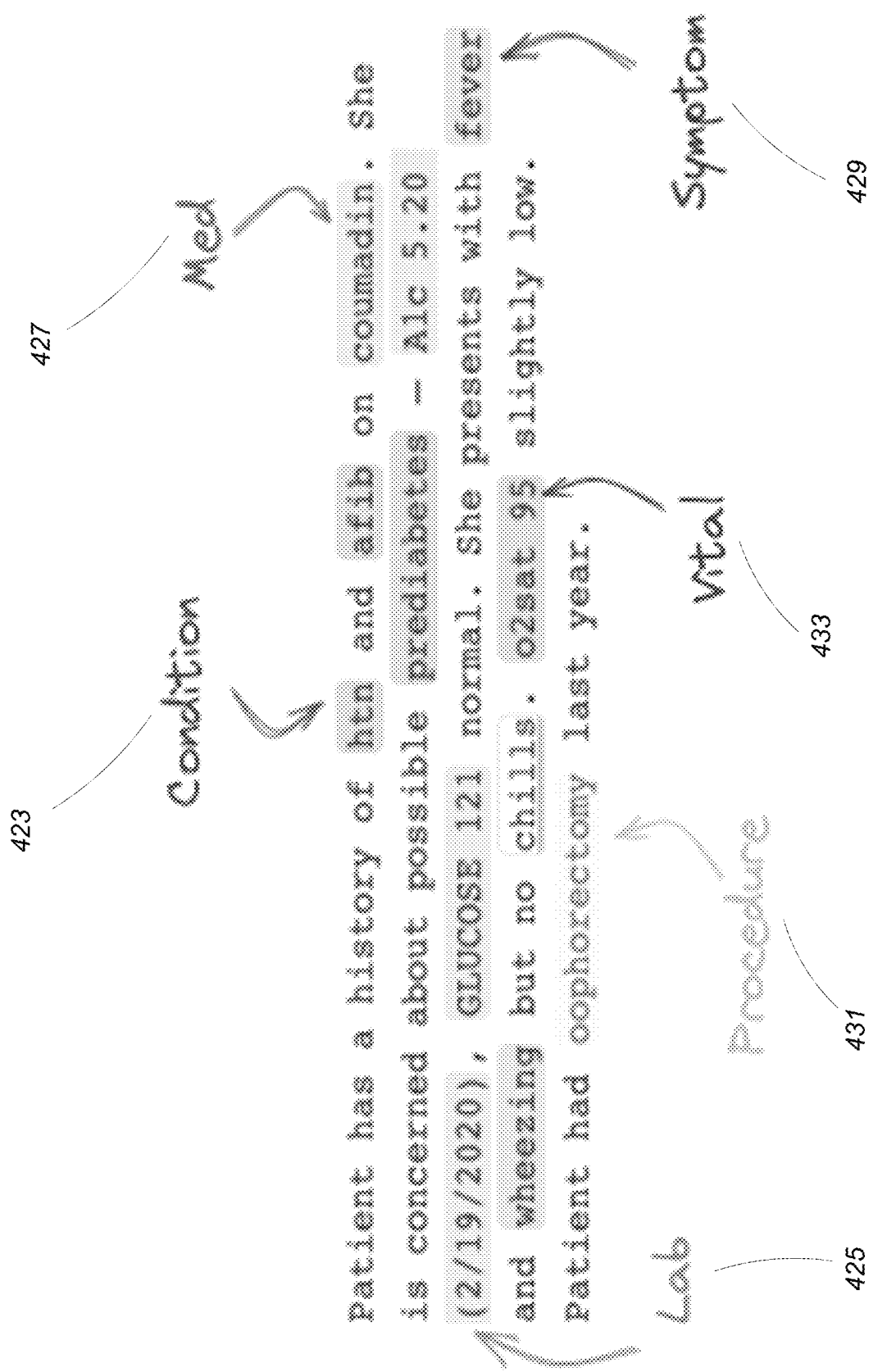
FIG. 5 shows highlighted semantic items in text.

Referring to FIGS. 4 and 5, in some examples, there are different types of semantic items are represented in the medical terminology database 112 such as conditions 423 (e.g., hypertension), lab results 425 (e.g., a GLUCOSE measurement), medications 427 (e.g., Tylenol), symptoms 429 (e.g., chest pain), procedures 431 (e.g., a hysterectomy), and vital signs 433 (e.g., systolic blood pressure). Different types of semantic items are highlighted differently (e.g., with different colors and/or labels) in the graphical user interface 104. For example, in FIG. 4, conditions 423 are highlighted using a first color or shading (e.g., red), lab results 425 are highlighted using a second color or shading (e.g., orange), medications 427 are highlighted using a third color or shading (e.g., green), symptoms 429 are highlighted using a fourth color or shading (e.g., purple), procedures 431 are highlighted using a fifth color or shading (e.g., yellow), and vital signs 433 are highlighted using a sixth color or shading (e.g., blue).

Referring to FIG. 6, in some examples, the different types of semantic items are derived from ontologies or other medical databases that define standard medical nomenclature. For example, semantic items related to conditions, symptoms, and procedures are derived from the SNOWMED CT ontology 635, semantic items related to medications are derived from the First Data Bank ontology 637, and semantic items related to lab results are derived from the LOINC database 639.

Semantic items are identified using the contextual autocomplete, post-recognition, and disambiguation techniques described below. Identified semantic items are displayed in the clinical note 207 and are interactive in that the user 102 can access additional information about a semantic item on "cards" by hovering over or clicking on the semantic item, also described below.

2.1.3 Contextual Autocomplete

Figure 7:
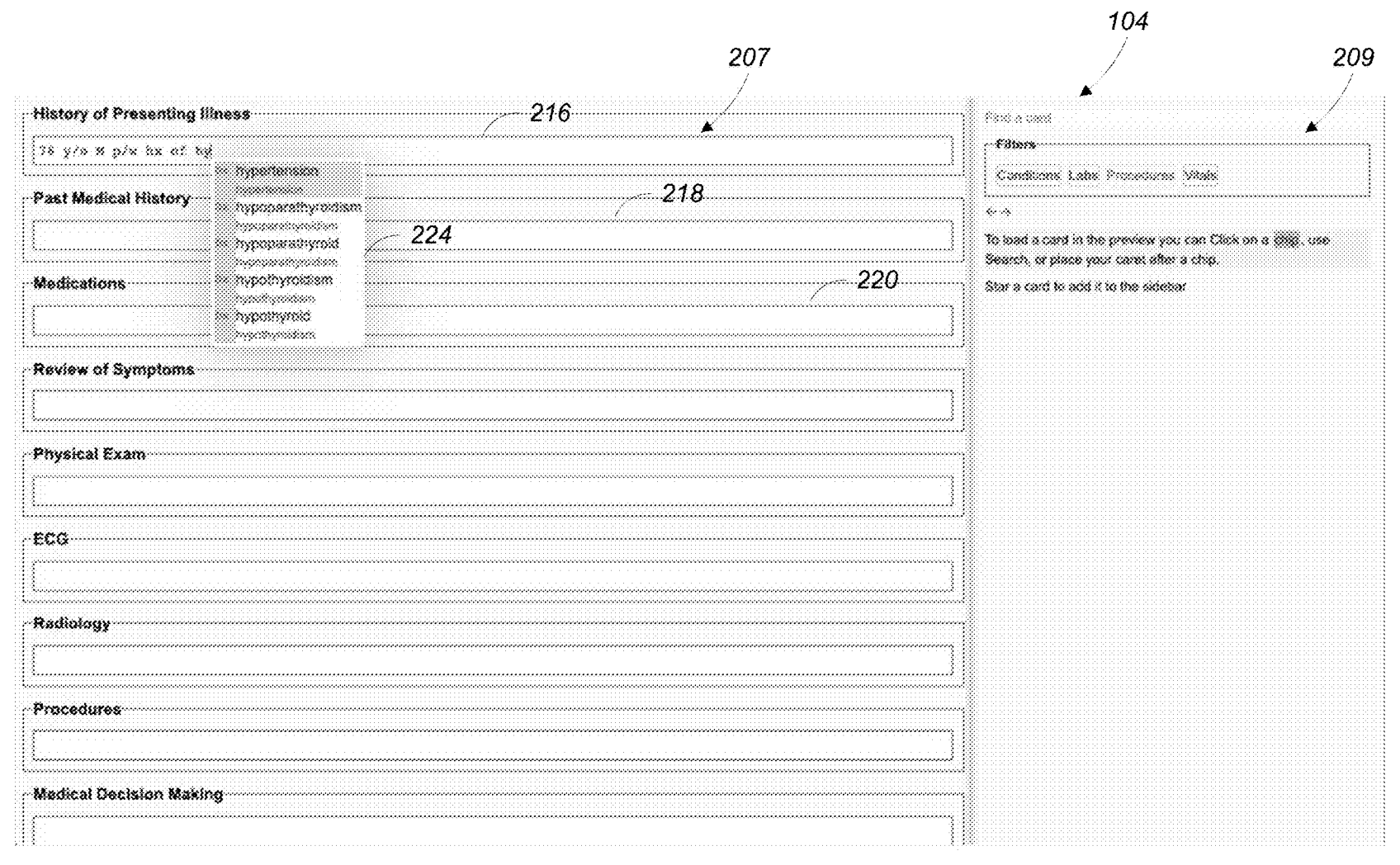

Referring to FIG. 7, the contextual autocomplete module 109 of FIG. 1 imparts contextual autocomplete functionality to the user interface 104. Generally, the contextual autocomplete functionality is implemented in the input processing module 108, which proactively identifies candidate semantic items from the medical terminology databases 112 as the user 102 enters text. The candidate semantic items are presented to the user 102 using a dropdown menu 224 in the graphical interface 104, where the user 102 can select one of the presented candidate semantic items for autocompletion.

In some examples, contextual autocomplete is triggered using rules based on phrases, word boundaries, and punctuation. For example, in FIG. 6 the user 102 types the phrase "hx of" in the "History of Presenting Illness" field 216, and a rule recognizes that the user is likely about to enter a condition. The rule triggers engagement of contextual autocomplete for the next letters typed by the user 102, where the context is that a condition is likely to be entered. With autocomplete engaged, when the user types the text "hy" after the phrase "hx of," the contextual autocomplete module 109 causes the input processing module 108 to access the medical terminology database 112 to determine candidate semantic items in the context of "conditions" for the input string "hy" (e.g., "hypertension," "hypothyroid," etc.).

In some examples, the contextual autocomplete module 109 predicts the candidate semantic items from the letters the user 102 has already entered, words present in the medical terminology databases 112, words previously entered by the user 102, words documented in earlier clinical notes (possibly by other users), and/or existing structured data (i.e., structured data from the current visit and earlier visits, such as laboratory test results, diagnosis and procedure codes, and problem lists). The prediction may be based on language modeling techniques where, within a set vocabulary (e.g., a set of clinical terms and their associated abbreviations and synonyms from medical ontologies such as the SNOMED and UMLS medical ontologies), the words most likely to occur are calculated. The prediction may also use frecency models and/or machine learning prediction (e.g., a one-dimensional convolutional neural network or a transformer autoregressive language model) techniques.

The candidate semantic items 224 are presented to the user 102 in the graphical user interface 104. In some examples, different types of candidate semantic items are displayed using different labels and/or colors. For example, semantic items may be marked with the label "Dx" and colored red if they represent a diagnosed condition. Similarly, a semantic item may be marked with the label "Lab" and colored orange if it represents a laboratory value.

In some examples, contextual autocomplete only displays candidate semantic items that are associated with a context of the rule that triggered contextual autocomplete (e.g., if the user enters "hx of," then only diagnosed condition semantic items are displayed). In other examples, candidate semantic items are ranked (e.g., ordered) based on the rule that triggered contextual autocomplete. In yet other examples, contextual autocomplete may be engaged using a trigger character (e.g., "/"), which allows the user to either force autocomplete to trigger or specify a clinical concept to rank first. For example, "/labs" or "/l" can be used to trigger an autocomplete context which is limited to labs. An empty slash forces autocomplete to trigger with the default ranking.

Figure 8:
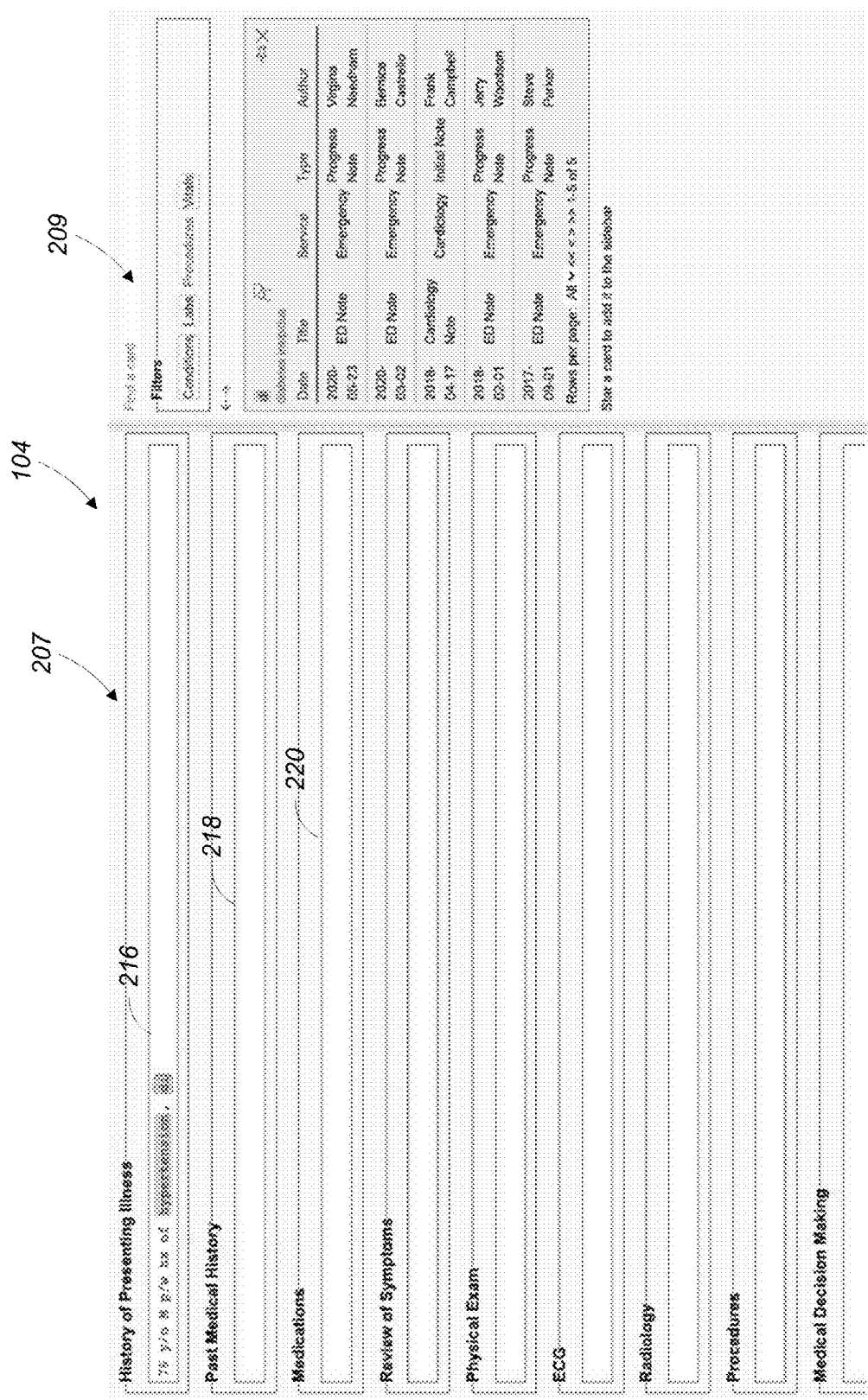
FIG. 8 shows an autocompleted semantic item.

Referring to FIG. 8, after the user 102 selects "hypertension" from the candidate semantic items, "hypertension" is populated and highlighted as a semantic item in the "History of Presenting Illness" field 216.

2.1.4 Post-Recognition

Figure 9:
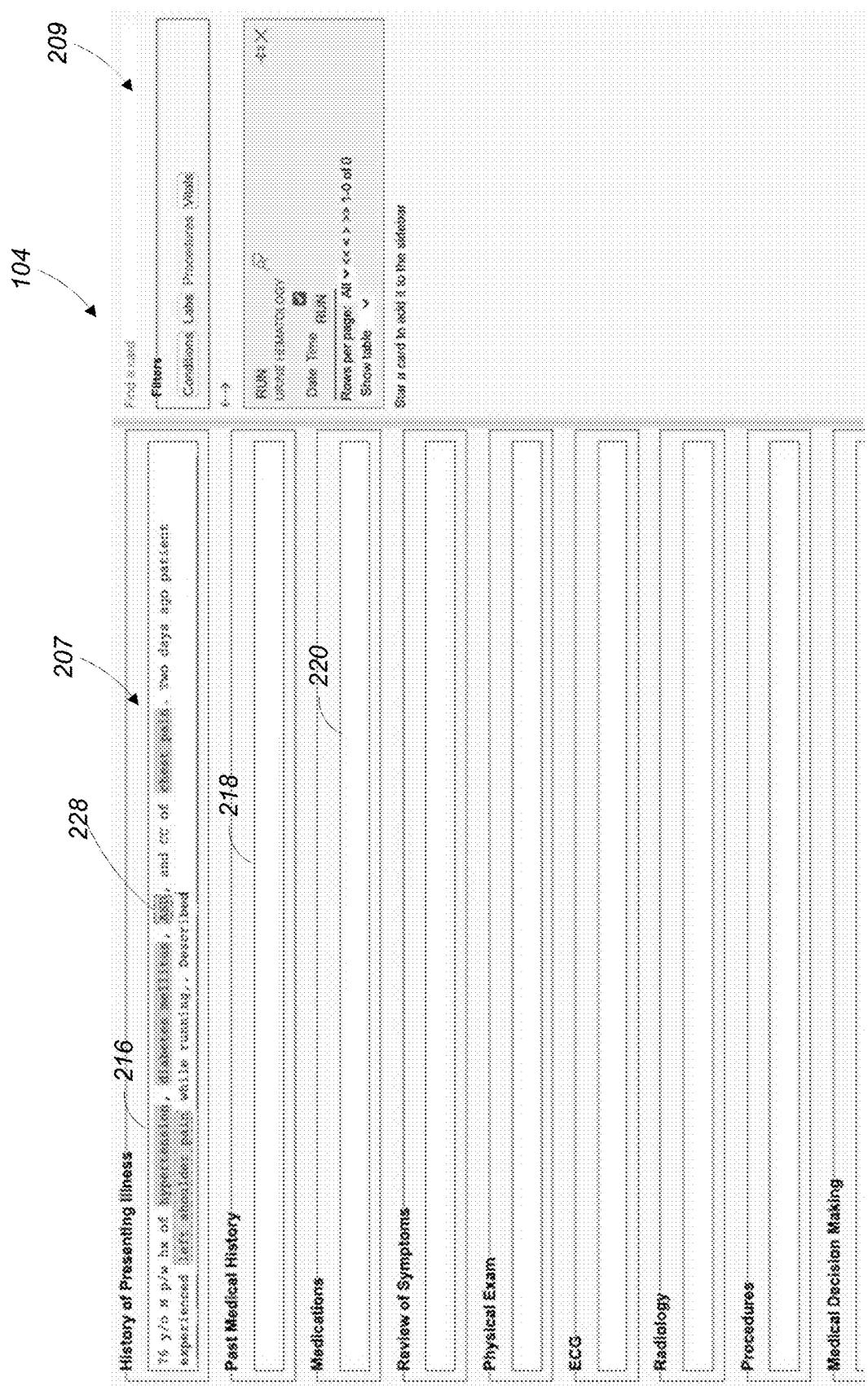
FIG. 9 shows a post-recognition functionality.

Referring to FIG. 9, in some examples, text is entered into the fields of the clinical note 207 without requiring the user to type the text. For example, the user can paste text into the fields or certain fields may be auto populated from the text in other fields. These alternative types of text entry do not trigger contextual autocomplete for recognizing semantic items in the text. Instead, the post-recognition module 111 (see FIG. 1) processes text entered outside of the autocompletion paradigm to automatically identify and highlight semantic items in the text. In some examples, the post-recognition module 111 implements a version of the Aho-Corasick string-searching algorithm to automatically identify clinical terms from the text that has already been typed and highlight them as semantic items. In other examples, the post-recognition module 111 uses machine learning methods in addition to or instead of the Aho-Corasick algorithm to identify clinical terms.

For example, in FIG. 9, as the user 102 continues entering text into the "History of Presenting Illness" field 216, certain text is not entered using autocomplete (e.g., by being pasted into the field). For example, after the user 102 pastes in text "diabetes mellitus, ASD, and CC of chest pain. Two days ago, patient experienced left shoulder pain while running . . . " the post-recognition module identifies and highlights clinical terms "diabetes mellitus," "ASD," "chest pain," and "left shoulder pain" as semantic items.

2.1.5 Disambiguation

Continuing to refer to FIG. 9, in some examples, a given post-recognized term may be ambiguous due to there being multiple possible clinical meanings associated with the term. For example, the term "ASD" may be interpreted as both a condition (i.e., atrial septal defect) and a lab value (i.e., a blood hematology lab value). Such ambiguous terms are discovered by the disambiguation module 113 indicated in the user interface (e.g., using a dashed line 228). In some examples, ambiguous clinical terms where all possible meanings of the term are of the same concept type are displayed with a color associated with that concept type. Where the possible meanings of an ambiguous term have different concept types, the color clinical terms are displayed with a gray coloration.

Figure 10:
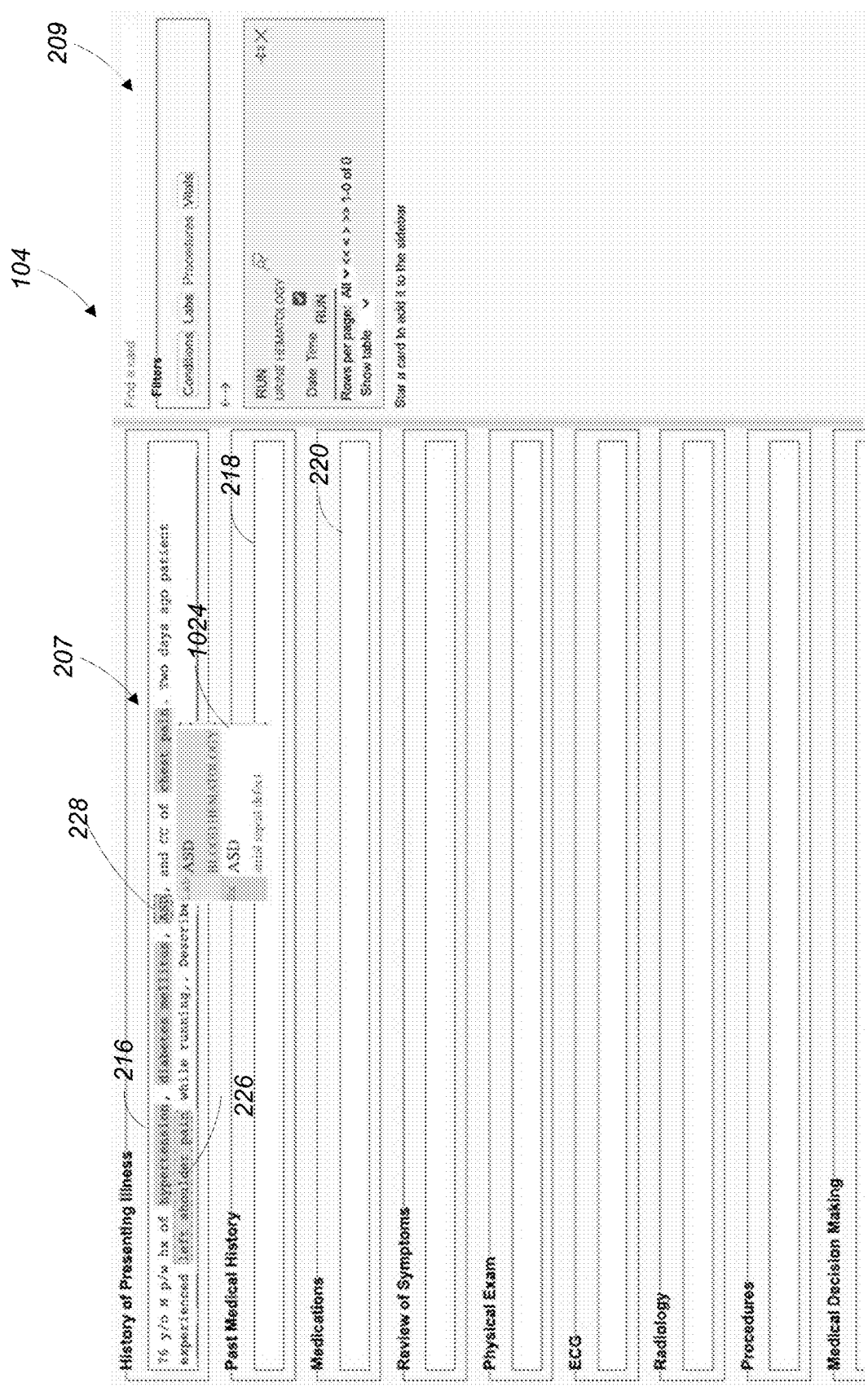
FIG. 10 shows a disambiguation functionality.

Referring to FIG. 10, the user 102 can select (e.g., "click") terms indicated as being ambiguous to access a disambiguation menu 1024. The disambiguation menu allows the user 102 to select an appropriate semantic item for the term from a list of possible semantic items.

2.1.6 Negation and Other Modifiers

Figure 11:
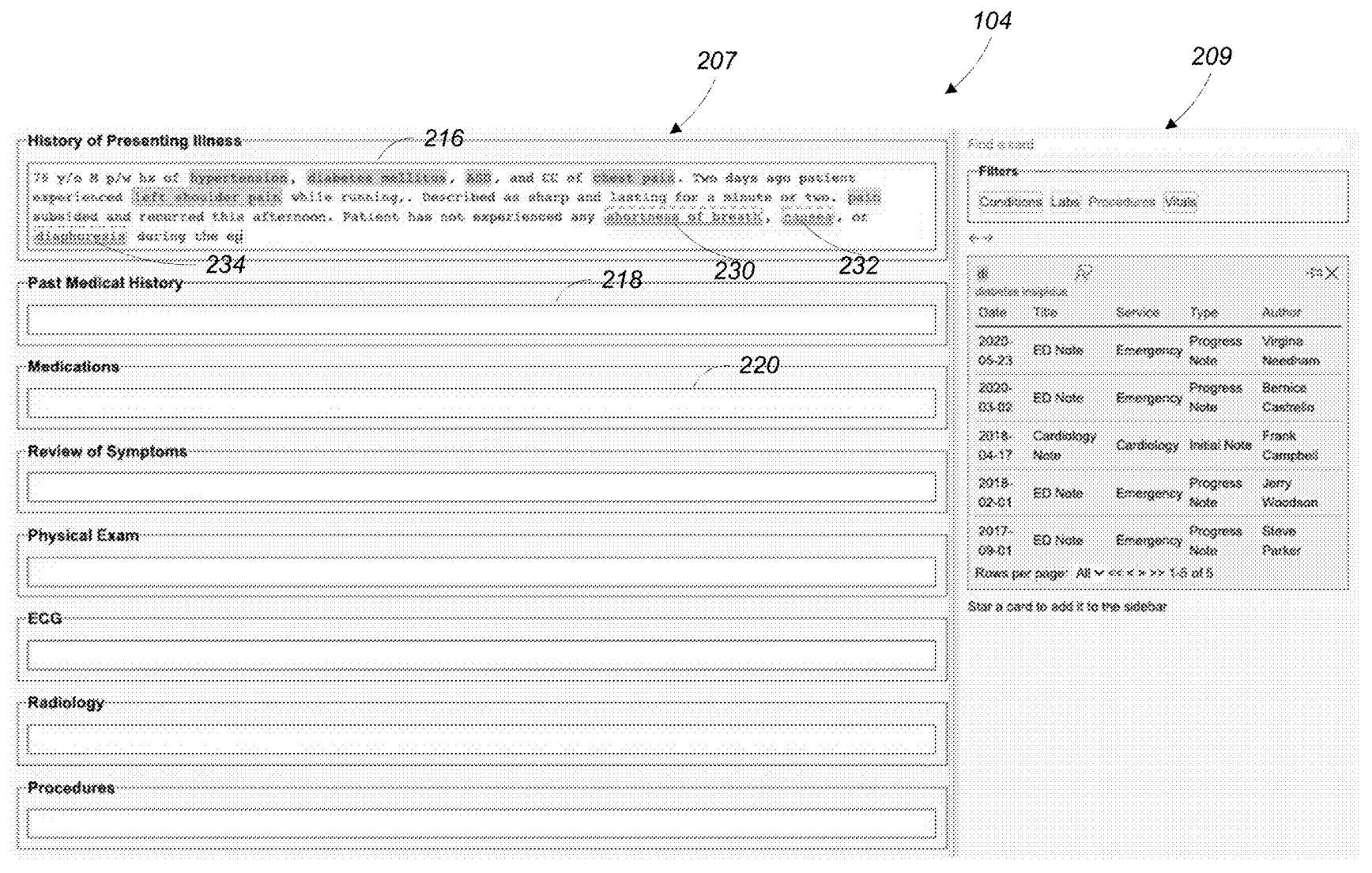

Referring to FIG. 11, in some examples, the modifier identification module 117 is configured to analyze the text in fields of the user interface 104 to identify modifiers such as negations in semantic items. For example, the user 102 may reference clinical terms to indicate the absence of something (e.g., "no fever"). In some examples, the modifier identification module 117 implements a modified version of the negex algorithm (or machine learning-based systems for identifying negations) for automatically identifying negated semantic items based on the surrounding text.

In FIG. 11, the user 102 has entered the text "Patient has not experienced any shortness of breath, nausea, or diaphoresis during . . . " The modifier identification module 117 processes the text to identify the semantic items "shortness of breath," 230 "nausea," 232 and "diaphoresis" 234 as symptoms that a patient has not experienced and identifies those terms as negations. The negations are shown as underlined semantic items in the graphical user interface 104.

Negations are just one type of modifier that can be identified by the modifier identification module 117. Other examples of modifiers that can be captured by the modifier identification module 117 include adjectives such as spatial orientation, body systems, severity, quantitative or temporal relations, third-party attribution, and uncertainty.

Another type of modifier than can be identified by the modifier identification module 117 is third-party attributions. For example, the term "family history of diabetes in mother" is an example of a third-party attribution modifier to "diabetes" because it indicates that the clinical concept of diabetes should not be assigned to the patient. Rule based or learned algorithms can be used to implement third-party attribution identification.

Another type of modifier that can be identified by the modifier identification module 117 is hedging. For example, the term "patient may have Lyme disease" is an example of hedging, where a clinician indicates uncertainty about a claim. Rule based or learned algorithms can be used to implement hedging identification.

2.1.7 Default Text Population

Figure 12:
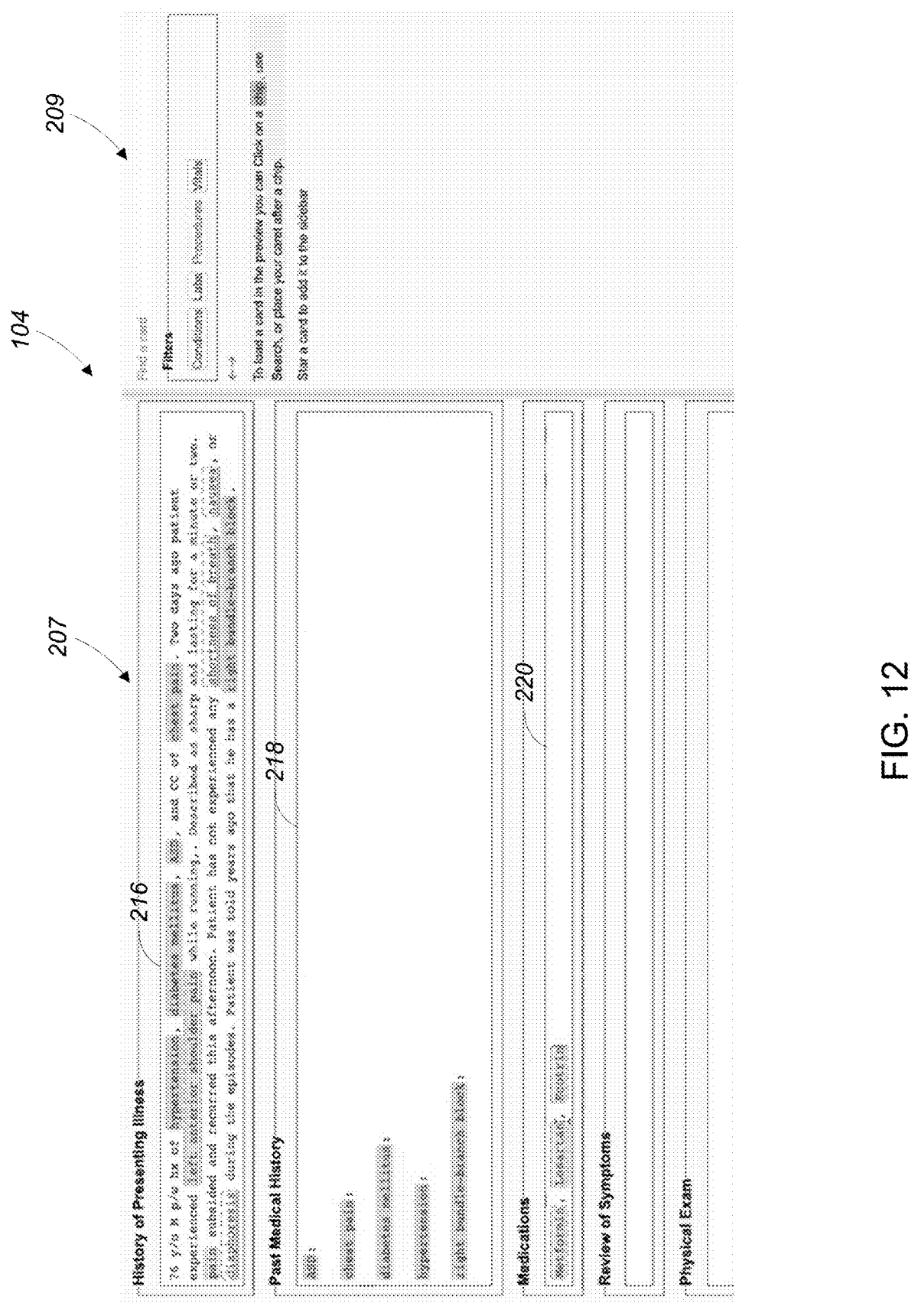

Referring to FIG. 12, in some examples, structured data captured in certain fields of the clinical note 207 is used by the clinical documentation system 100 to fill in other fields of the clinical note. For example, each field may be associated with a template based on expected clinician input. When the user clicks on into a blank field with such a template, the field is auto-populated with the template text constructed using a mix of structured information parsed from the electronic health record as well as clinical terms previously captured in the clinical note 207 as semantic items.

For example, in FIG. 12 semantic items from the "History of Presenting Illness" field 216 are used to populate the "Past Medical History" and "Medications" fields 218, 220. In doing so, the semantic terms are copied from one field to the other, where the "Past Medical History" field 218 is filled with semantic terms from the "History of Presenting Illness" field 216 (e.g., "ASD," "chest pain," etc.). In other examples, the fields are populated from the patient's EHR 106. For example, in FIG. 12 when a user clicks in the "Medications" field 220, the data retrieval module 110 accesses the EHR 106, identifies the patient's medications (e.g., "Metformin," "Losartan," and "Ecotrin"), and automatically populates the "Medications" field 220 with semantic items for the identified medications.

Referring to FIG. 13, another example of default text population includes populating a review of Systems (ROS) section 1350, which is a boilerplate list of ten clinically relevant systems. For each system the user is tasked with describing the presence or lack of symptoms related to that system. The input processing module 108 interacts with the user interface 104 and the data retrieval module 110 to automatically generate the ROS text for the user from text already entered in other fields of the user interface (e.g., when a symptom is documented in another field of the clinical note, it is added to the appropriate line of the ROS template).

In some examples, clarifying modifiers and specifiers (e.g., the "left" and "lower" in "left lower abdominal pain") are carried along with clinical terms identified as semantic items when populating default text. One technique for doing so is to use greedy algorithm to attach modifiers as prefixes to clinical concepts. Other techniques include more advanced natural language processing methods.

2.1.8 Context Specific Information Retrieval

Figure 14:
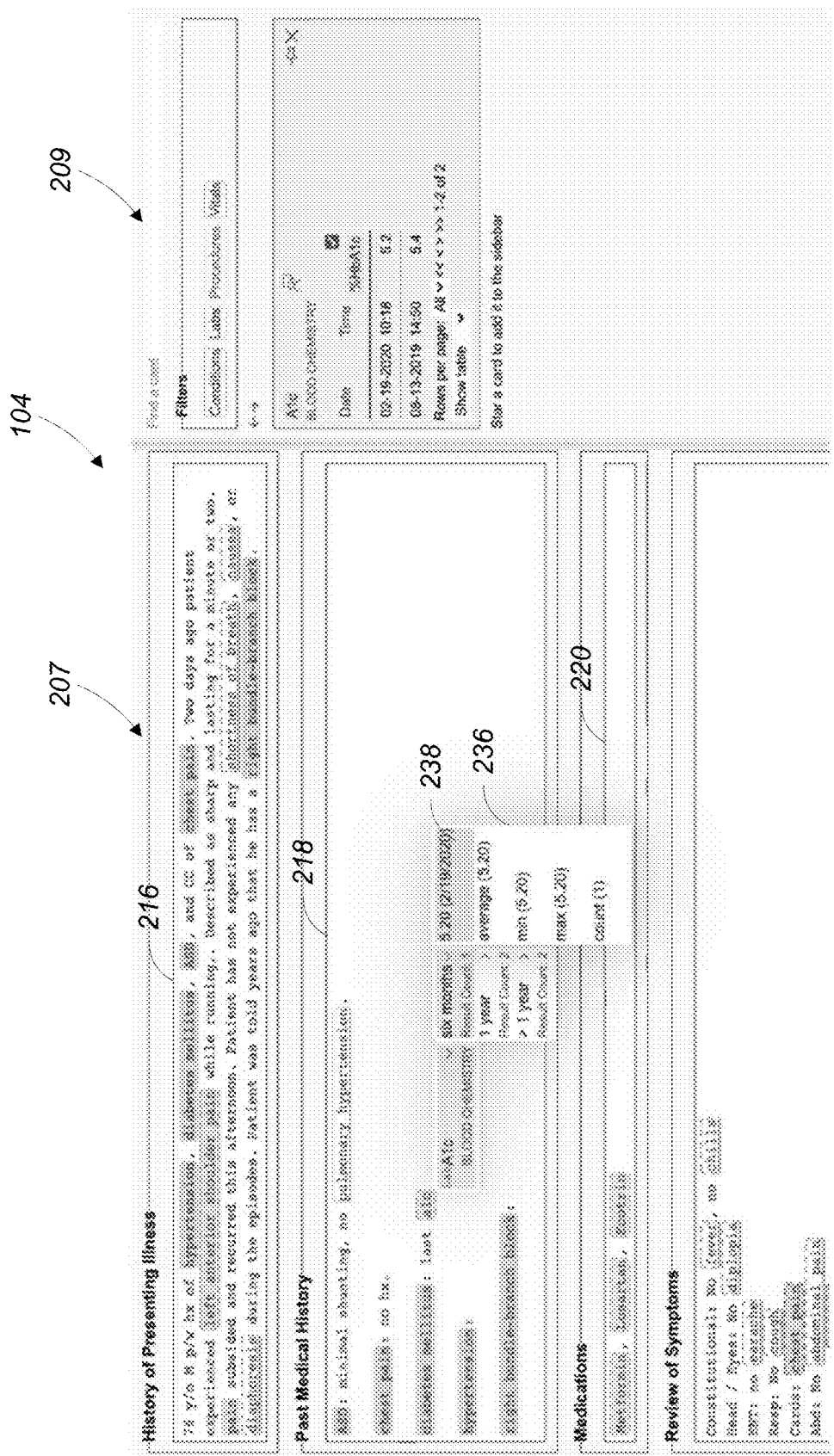
FIG. 14 shows context-specific autocompletion of data from an EHR.

Referring to FIG. 14, in some examples the contextual autocomplete module 109 automatically retrieves additional context-specific information from the patient's EHR 106 for a particular semantic item when populating the clinical note 207 with the semantic item. The additional information is presented as a tree of menus that the user 102 can navigate to further populate the clinical note with information from the patient's EHR. This hierarchical menu can be used to insert structured data associated with an autocompleted semantic item. For example, the user can select the name of the lab, a time frame based aggregate, or individual statistics within a time frame.

For example, in FIG. 14, the user 102 has interacted with a semantic item for the A1c blood chemistry lab, causing a tree-based lab selection menu 236 to appear. The menu 236 is populated with past lab values from the patient's EHR. The user drills down through the menu to select a lab value 238 from Feb. 19, 2020, which is then inserted into the relevant field of the clinical note 207.

In some examples, items in the autocomplete dropdown menu are labeled with "in patient medical record" when they are derived from the patient's EHR. Other labeling techniques may be used.

3 Sidebar

As is mentioned above, the sidebar 209 is used to present pertinent clinical information to the user 102 as the user interacts with the user interface 104 to, for example, complete the clinical note 207. In general, user interface elements referred to as "cards" are displayed in the sidebar 209. The sidebar allows the user 102 to search for particular cards, pin cards to the sidebar, filter cards shown in the sidebar (e.g., by context type), and navigate through pinned cards. In some examples, pinned cards persist in the user interface 104 so both the user 102 and clinicians other than the user are shown persisted cards when they view the user interface 104. The persistence feature facilitates clinician communication through the user interface 104.

3.1 Cards

In general, cards provide concept-oriented information about a particular semantic item. For example, condition cards display relevant medications from the patient's medical record, relevant vital signs, related procedures, and relevant snippets from notes in the patient's medical record. Labs and vitals cards display box and whisker charts of lab values. Procedures and Medications cards contain a list of relevant note snippets from the patient's medical history. In some examples, note snippets are surfaced if they contained a mention of the semantic item or a closely linked semantic item and are ordered chronologically.

Figure 15:
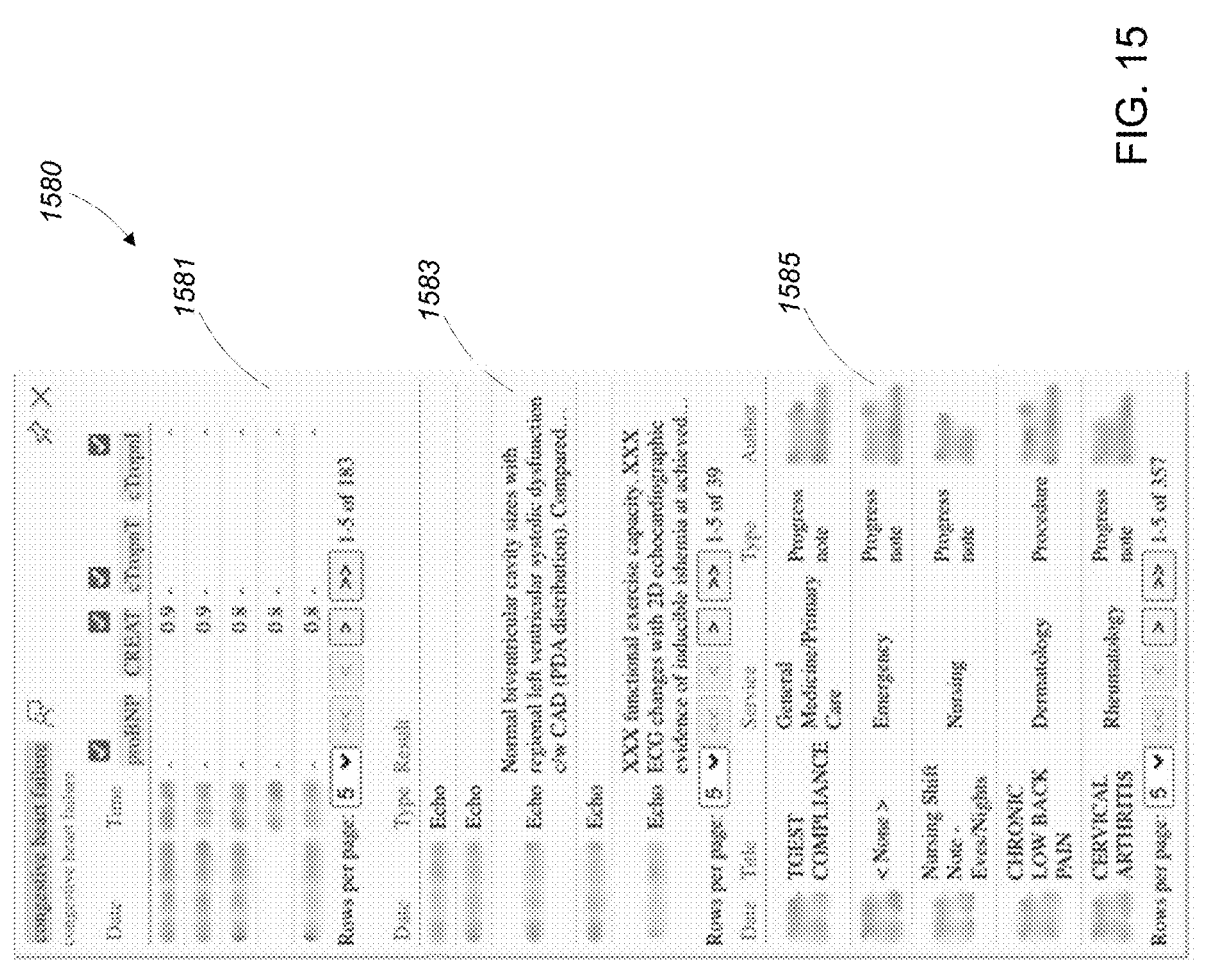

For example, referring to FIG. 15, a card 1580 for the "congestive heart failure" semantic item displays information from the patient's EHR that is relative to the congestive heart failure condition. For example, the card displays lab values 1581 for the patient, vital sign data 1583 for the patient, and notes 1585 related to the patient's condition.

3.1.1 Card Surfacing

Figure 16:
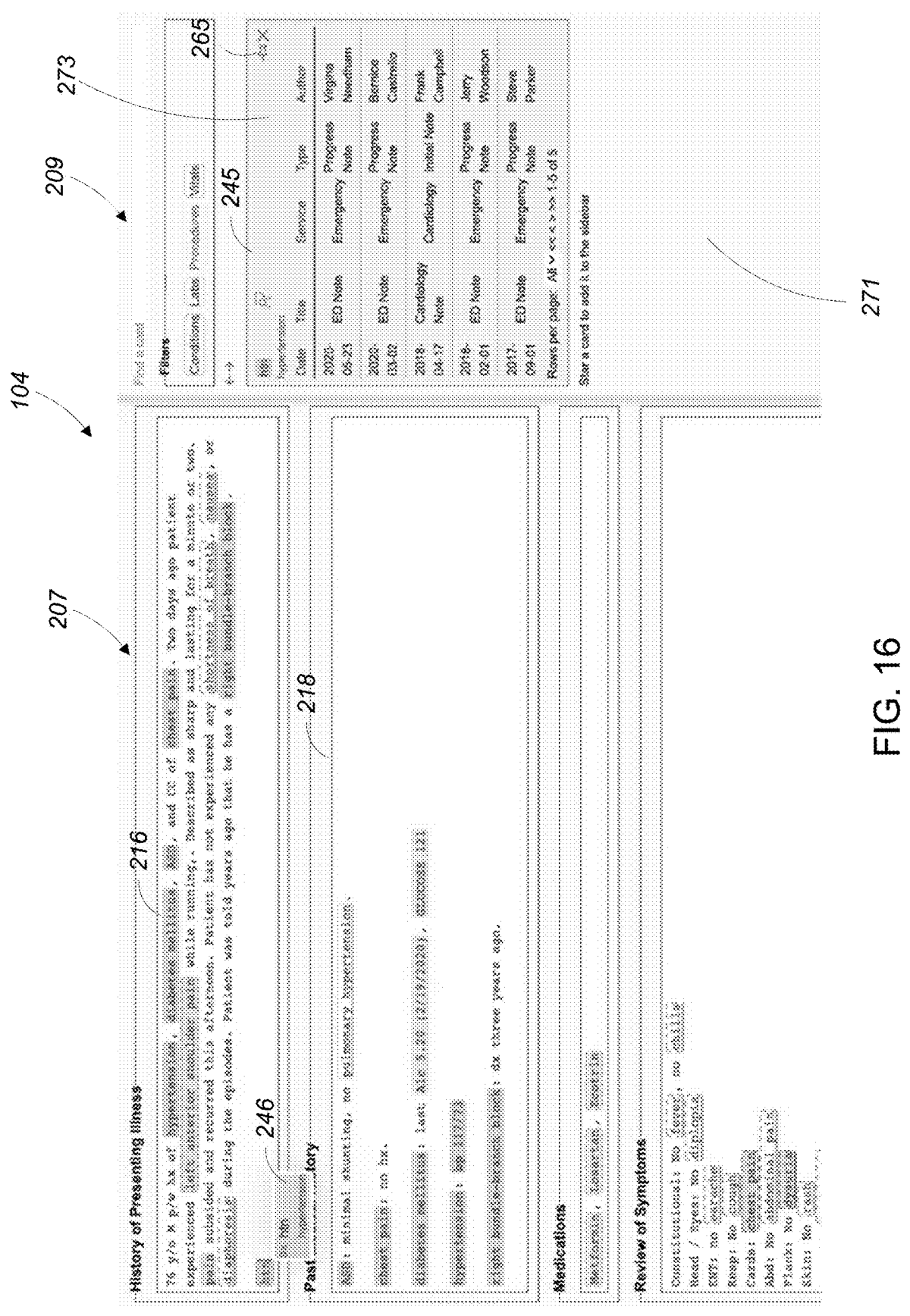

Referring to FIG. 16, in some examples, the sidebar 209 includes a preview pane 273 and a persistent pane 271. In general, as the user 102 enters text that activates autocomplete or interacts with a post-recognized semantic item, a card for the relevant semantic item is displayed in the preview pane 273. In some examples, the preview pane 273 displays one card at a time, and the card is not shared between users. If the user finds the card in the preview pane particularly useful, they can pin to move it to the persistent pane 271.

For example, in FIG. 16, the user 102 is interacting with a currently being typed, autocompleted, or post-recognized semantic item for hypertension ("htn"). The semantic item is presented to the user in a dropdown menu 246 and a card 245 for the htn semantic item is presented in the preview pane 273 of the sidebar 209. Clicking the "pin" button 265 on the card 245 would cause the card to be persistently pinned in the persistent pane 271 (e.g., in an area below the preview pane).

Figure 17:
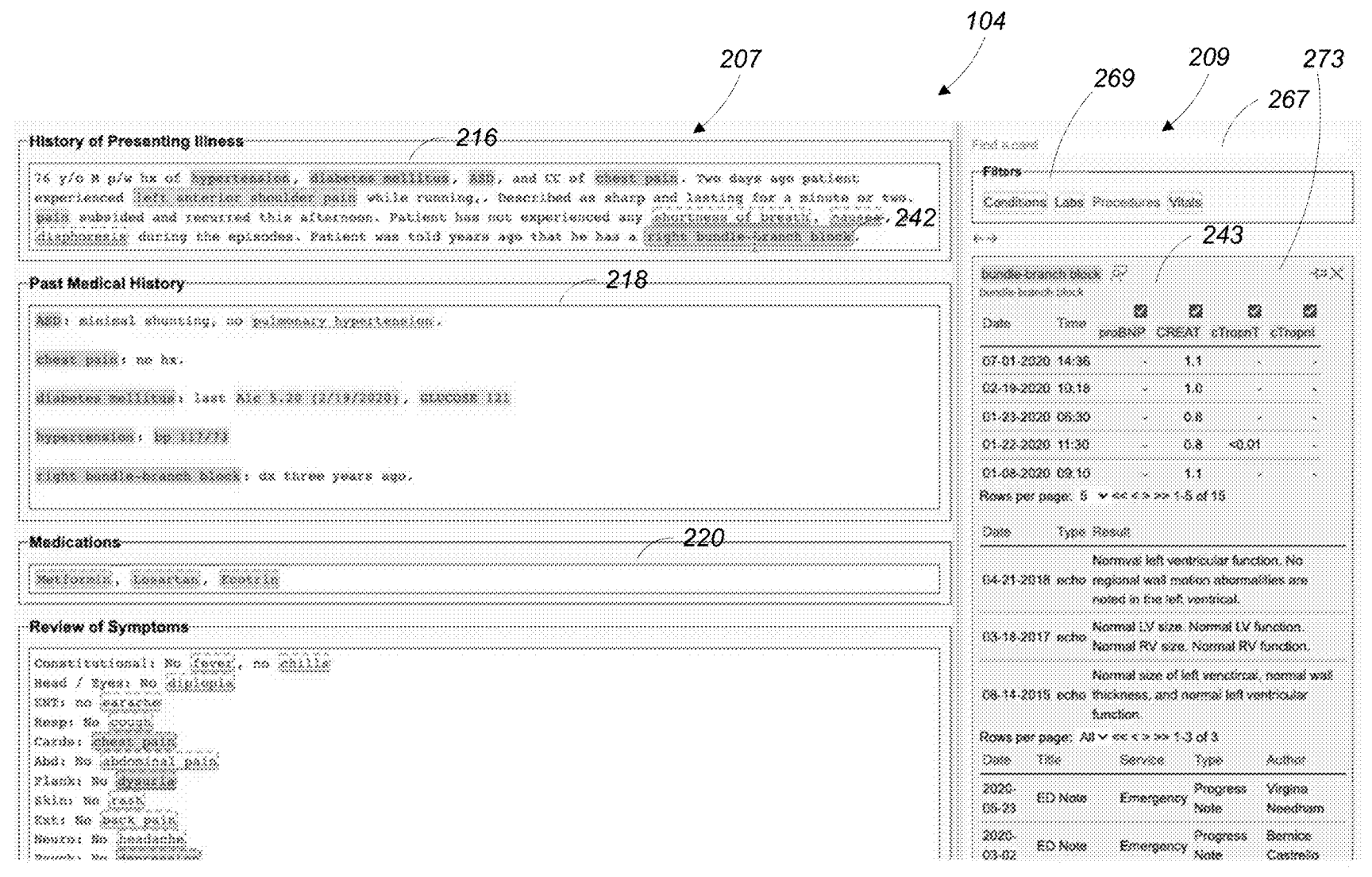

Referring to FIG. 17, in other examples, a semantic item already present in a field of the clinical note 207 can be clicked to cause an information card for the semantic item to be displayed in the preview pane 273. For example, in FIG. 17 the user 102 clicks on the "right bundle-branch block" semantic item 242 and an informational card 243 providing detailed patient information for the clicked the semantic item 242 is shown in the preview pane 273. Again, the user 102 can "pin" the card to cause it to be persistently present in the persistent pane 271.

In some examples, the user 102 can search for cards in the sidebar 209 using a keyword search field 267 or filter the cards in the sidebar by context using a filter menu 269.

3.1.2 Inline Card Surfacing

Figure 18:
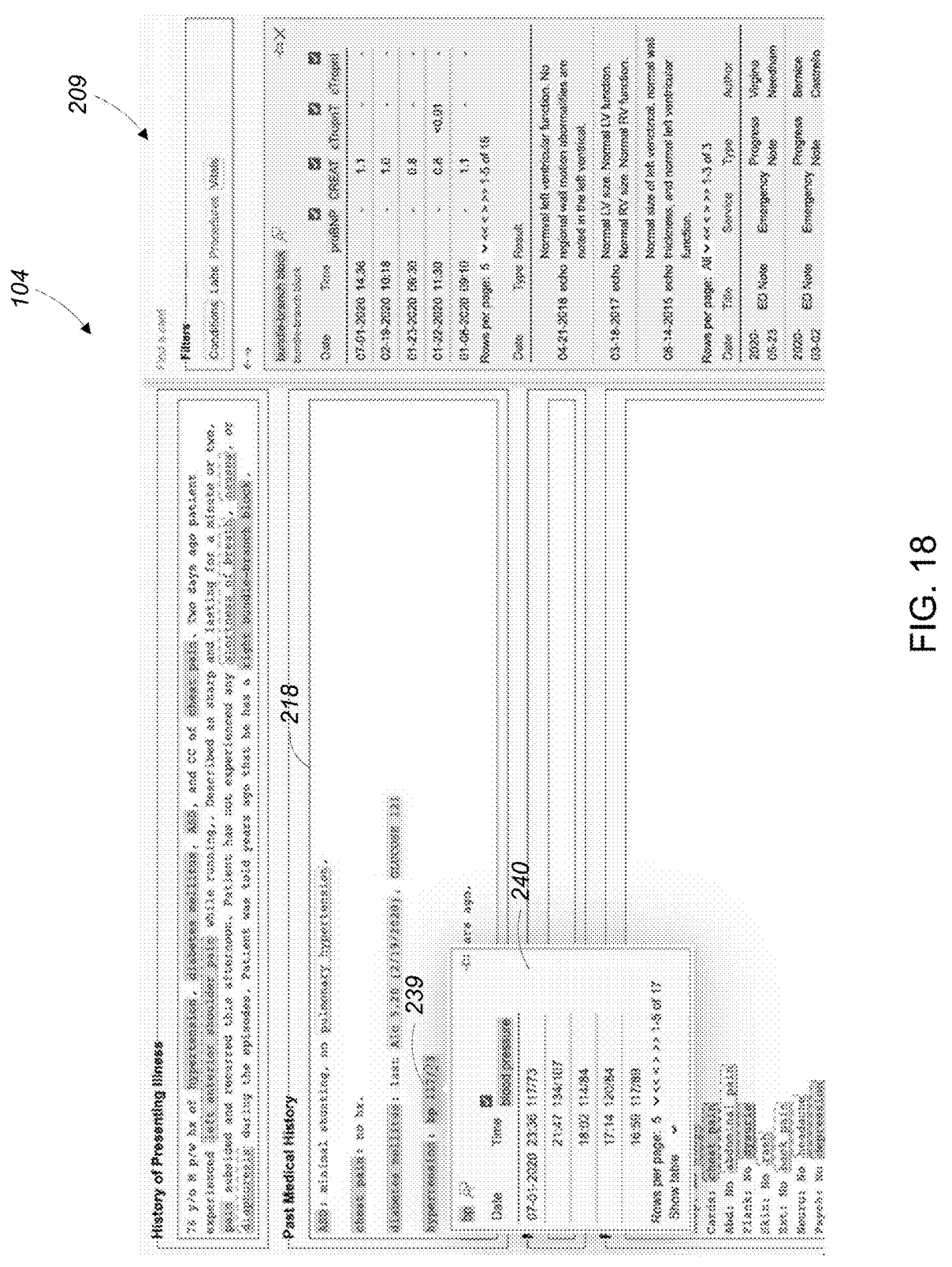

Referring to FIG. 18, in some examples, the user 102 can hover over a semantic item to cause a card associated with the semantic item to appear in an area near the semantic item. For example, in FIG. 18, the user 102 hovers over the "bp 117/73" semantic item 239 and a popup 240 appears showing a card with a history of blood pressure measurements from the patient's history (gleaned from the patient's EHR 106).

3.1.3 Card Design

In some examples, the user interface 104 includes a default set of cards specifically designed for certain common clinical concepts. However, certain clinicians may require that different information is displayed on cards for common clinical concepts. Furthermore, less common clinical concepts may require development of new cards by clinicians.

Figure 19:
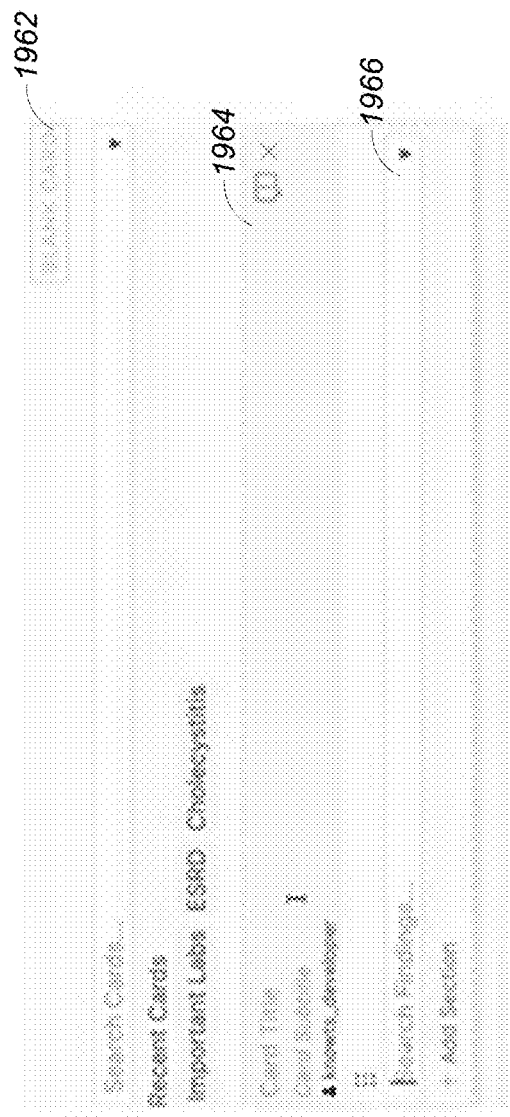
FIG. 19 shows a first step in a card design process.
Figure 20:
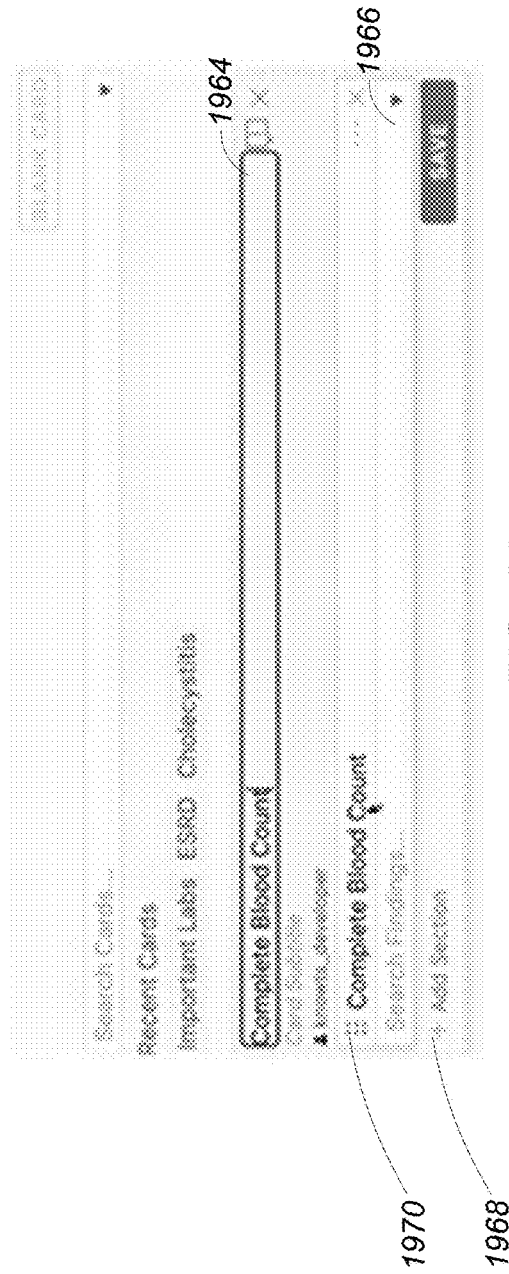
FIG. 20 shows a second step in a card design process.

Referring to FIG. 19, the user 102 can create their own card by clicking a "blank card" button 1962, which causes "Card Title" 1964 and "Search Findings" 1966 fields to appear. Referring to FIG. 20, the user gives a name to their card by filling the "Card Title" field 1964 (e.g., with the card name "Complete Blood Count"). The user also adds a new section 1966 to the card (e.g., by clicking the "Add Section" button 1968 and titles the section "Complete Blood Count."

Figure 21:
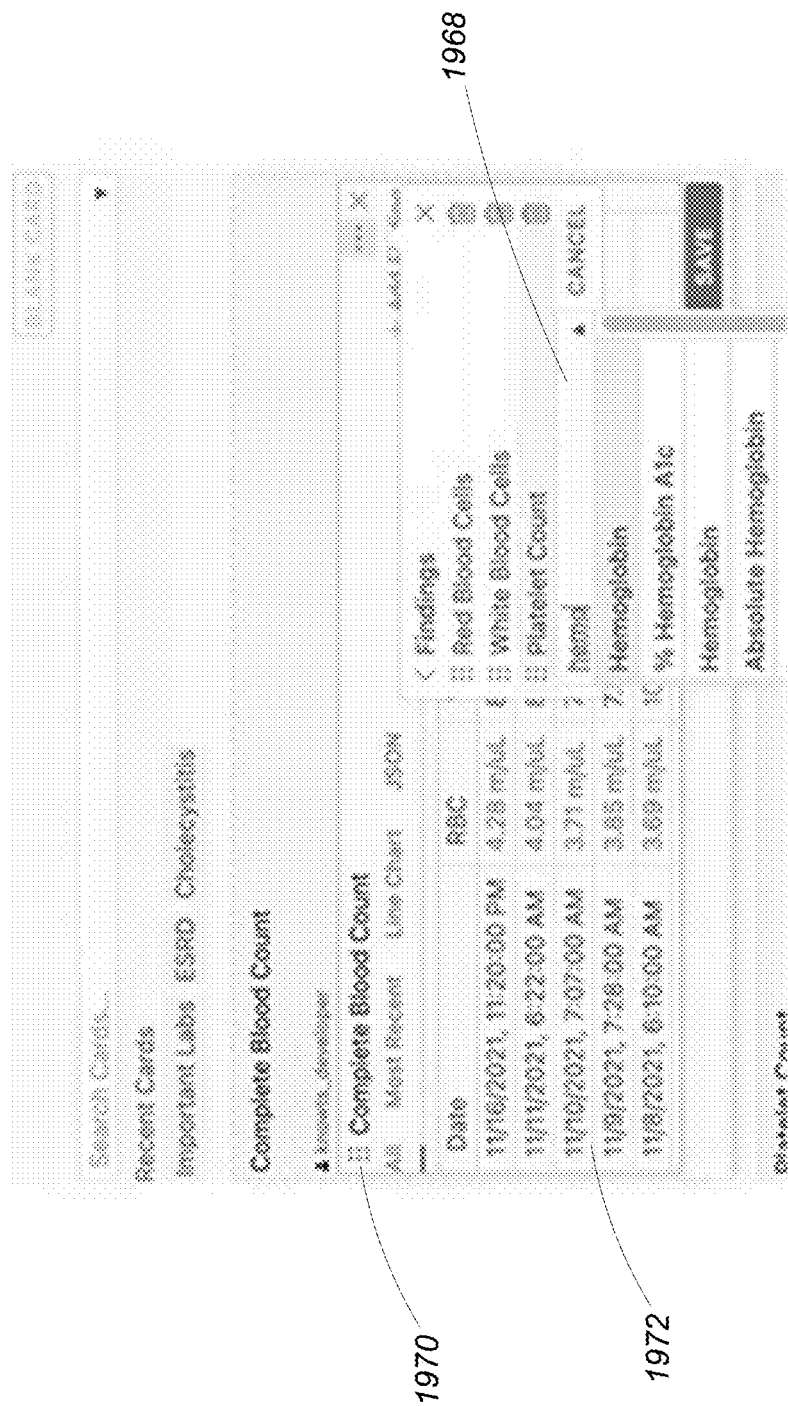
FIG. 21 shows a third step in a card design process.
Figure 22:
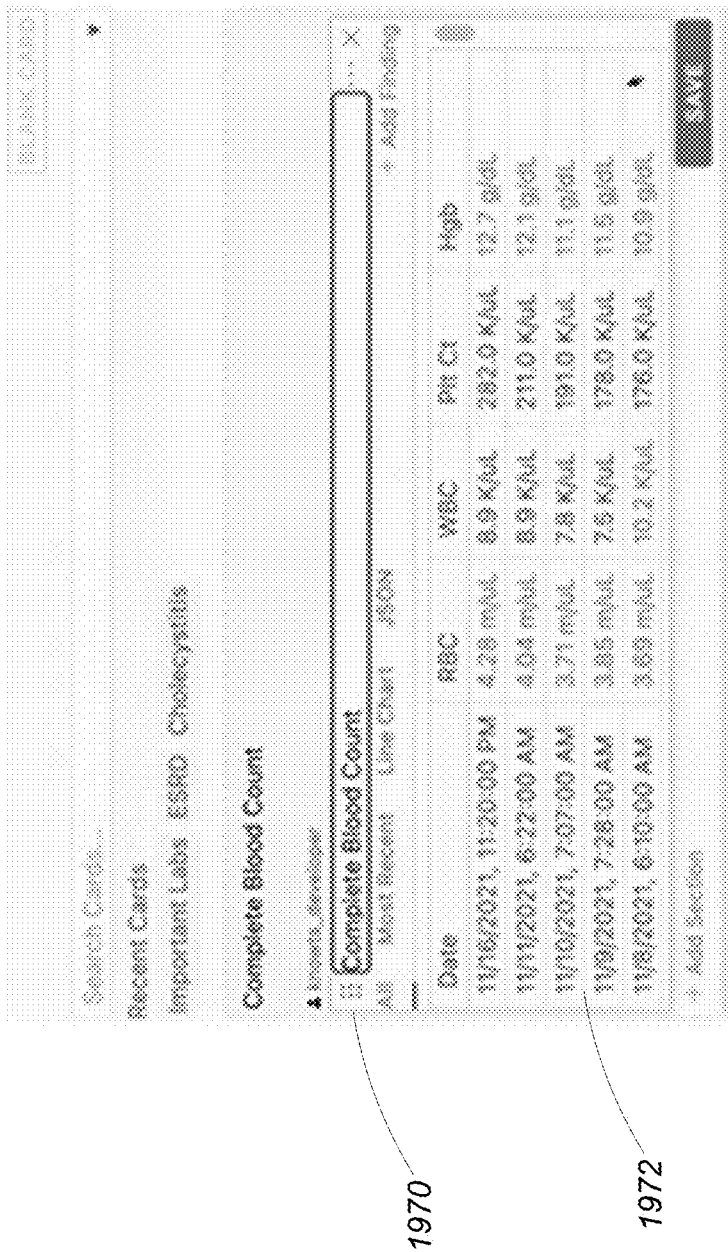
FIG. 22 shows a custom designed card with a grid view.
Figure 23:
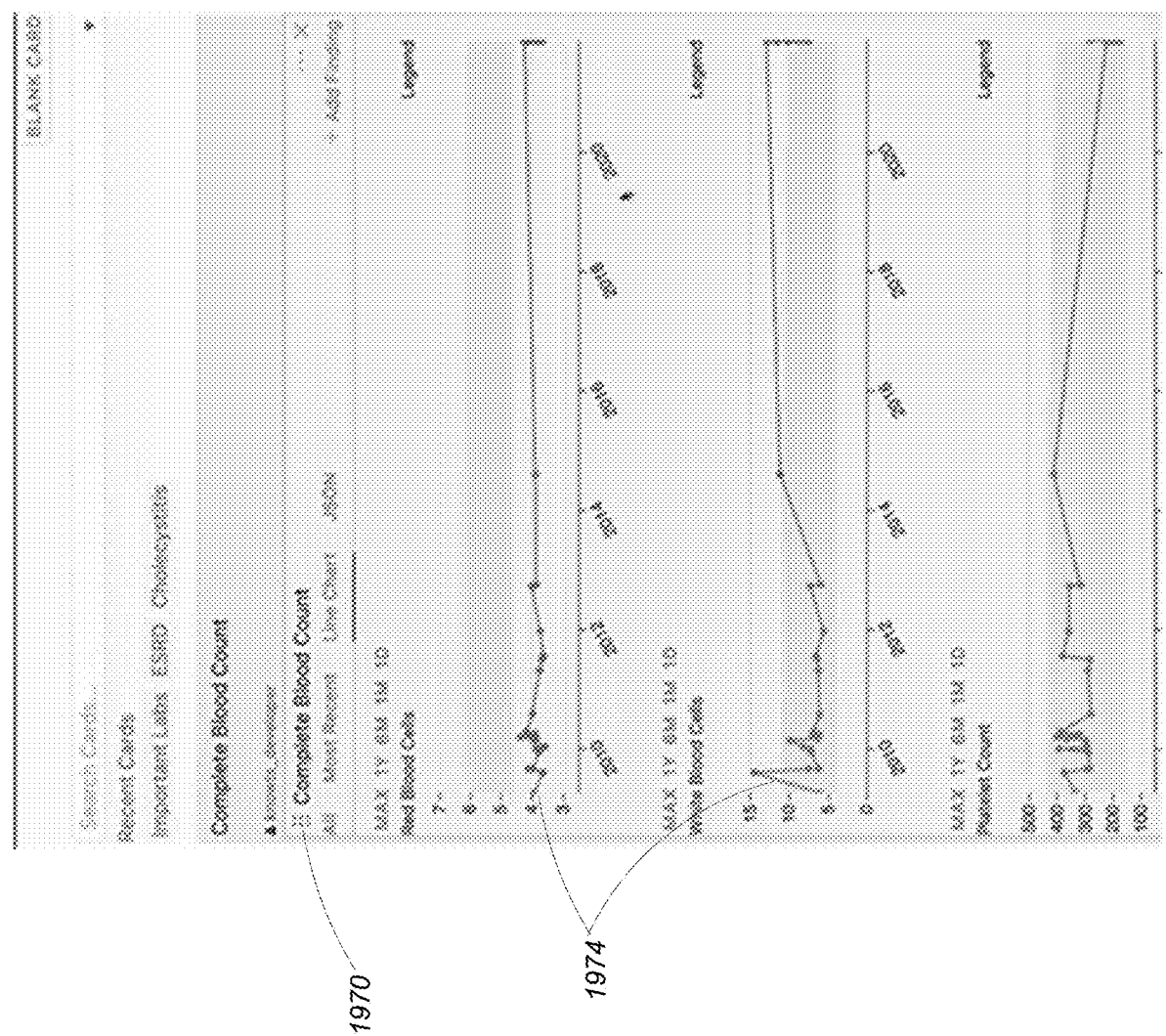
FIG. 23 shows a custom designed card with a line chart view.

Referring to FIGS. 21 and 22, the user 120 then uses the "Search Findings" field 1968 to add data to the "Complete Blood Count" section 1970 of the card. In this example, the user adds "Red Blood Cells," "White Blood Cells," "Platelet Count," and "Hemoglobin" labs to the "Complete Blood Count" section 1970 of the card. In FIG. 22, a time series of the added lab values are shown in a grid 1972. Referring to FIG. 23, in some examples, alternative views of the added lab values are available, such as line chart views 1974 of the lab values.

In general, once created, a new card is added to a repository that is available to other users and is associated with a semantic item that can be recognized by the user interface 104.

Figure 24:
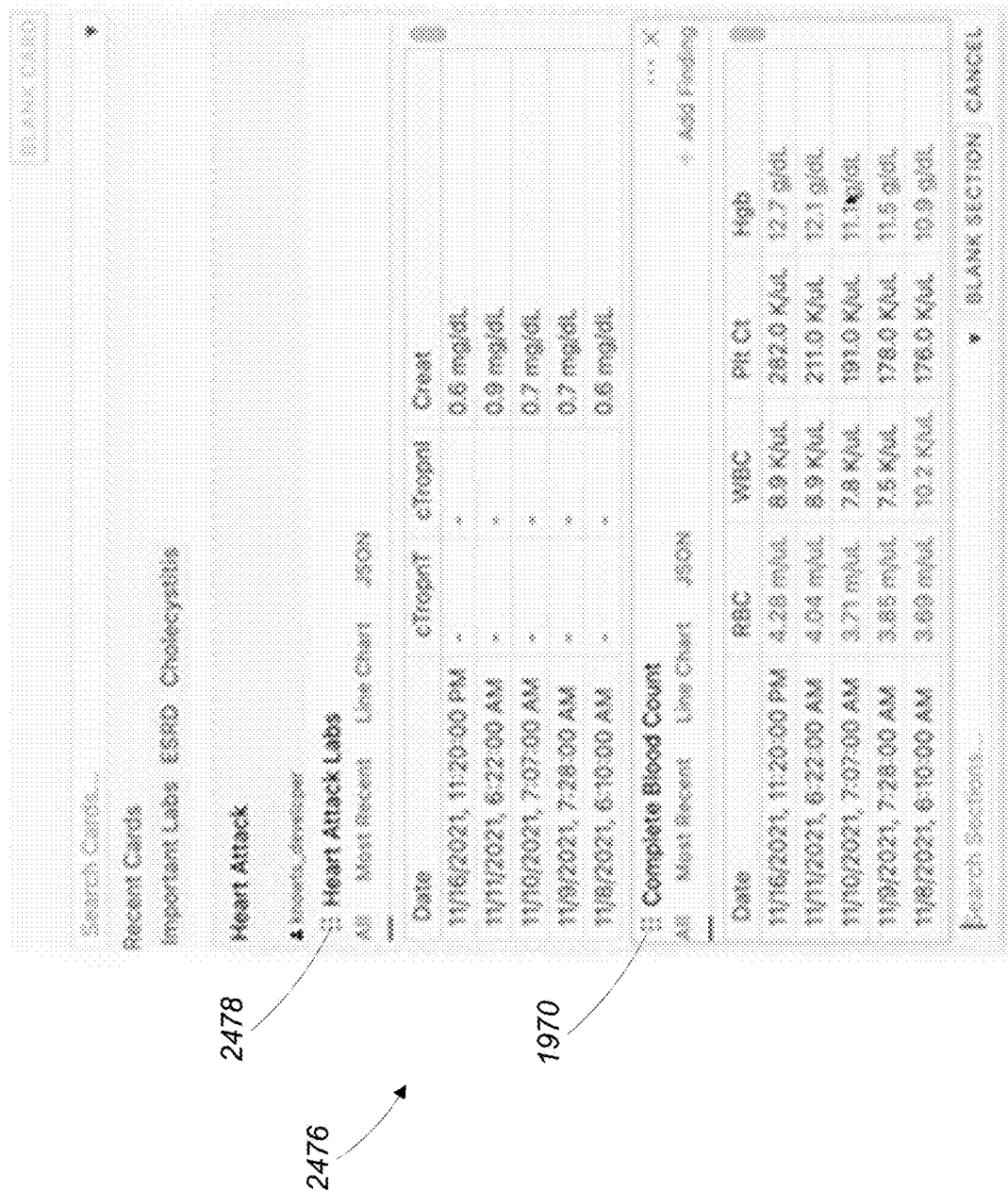
FIG. 24 shows a section of a custom designed card nested in another custom designed card.

Referring to FIG. 24, cards can also be added as sections to other cards. For example, in FIG. 24, the "Heart Attack Labs" card 2476 has a "Heart Attack Labs" section 2478 and also has a section created by inserting the "Complete Blood Count" labs section 1970 developed in FIGS. 19-23 as a new section into the card. In this way cards can be "bundled" together to created nested cards.

In some examples, cards may also be configured to compute values or indicators from various lab values (e.g., a formula may be applied to several lab values and the result may be used to flag when a patient has a condition).

4 Alternatives

Aspects described herein can be used in any number of clinical settings including emergency room settings, inpatient settings, outpatient settings. Other settings where aspects can be used include telemedicine providers, specialty clinics, urgent care clinics, and pharmacies.

5 Implementations

The approaches described above can be implemented, for example, using a programmable computing system executing suitable software instructions or it can be implemented in suitable hardware such as a field-programmable gate array (FPGA) or in some hybrid form. For example, in a programmed approach the software may include procedures in one or more computer programs that execute on one or more programmed or programmable computing system (which may be of various architectures such as distributed, client/server, or grid) each including at least one processor, at least one data storage system (including volatile and/or nonvolatile memory and/or storage elements), at least one user interface (for receiving input using at least one input device or port, and for providing output using at least one output device or port). The software may include one or more modules of a larger program, for example, that provides services related to the design, configuration, and execution of a program. The modules of the program can be implemented as data structures or other organized data conforming to a data model stored in a data repository.

The software may be stored in non-transitory form, such as being embodied in a volatile or non-volatile storage medium, or any other non-transitory medium, using a physical property of the medium (e.g., surface pits and lands, magnetic domains, or electrical charge) for a period of time (e.g., the time between refresh periods of a dynamic memory device such as a dynamic RAM). In preparation for loading the instructions, the software may be provided on a tangible, non-transitory medium, such as a CD-ROM or other computer-readable medium (e.g., readable by a general or special purpose computing system or device), or may be delivered (e.g., encoded in a propagated signal) over a communication medium of a network to a tangible, non-transitory medium of a computing system where it is executed. Some or all of the processing may be performed on a special purpose computer, or using special-purpose hardware, such as coprocessors or field-programmable gate arrays (FPGAs) or dedicated, application-specific integrated circuits (ASICs). The processing may be implemented in a distributed manner in which different parts of the computation specified by the software are performed by different computing elements. Each such computer program is preferably stored on or downloaded to a computer-readable storage medium (e.g., solid state memory or media, or magnetic or optical media) of a storage device accessible by a general or special purpose programmable computer, for configuring and operating the computer when the storage device medium is read by the computer to perform the processing described herein. The inventive system may also be considered to be implemented as a tangible, non-transitory medium, configured with a computer program, where the medium so configured causes a computer to operate in a specific and predefined manner to perform one or more of the processing steps described herein.

A number of embodiments of the invention have been described. Nevertheless, it is to be understood that the foregoing description is intended to illustrate and not to limit the scope of the invention, which is defined by the scope of the following claims. Accordingly, other embodiments are also within the scope of the following claims. For example, various modifications may be made without departing from the scope of the invention. Additionally, some of the steps described above may be order independent, and thus can be performed in an order different from that described.

What is claimed is:

1. A computer implemented method for managing medical information, the method comprising:
   displaying a plurality of user interface elements within a graphical user interface;
   receiving medical information for a patient in a first user interface element of the plurality of user interface elements;
   processing the medical information to identify one or more semantic items, the one or more semantic items including a first semantic item;
   processing a medical record for the patient according to the first semantic item, the processing including identifying a plurality of medical information items related to the first semantic item; and
   presenting at least some medical information items of the plurality of medical information items in a second user interface element configured to display medical information items related to the first semantic item.

2. The method of claim 1 further comprising parsing an electronic health record for the patient to identify the plurality of medical information items.

3. The method of claim 1 wherein the medical information for the patient includes textual input.

4. The method of claim 3 wherein receiving the medical information for the patient includes processing the textual input as it is entered to present one or more predicted semantic items associated with the textual input.

5. The method of claim 4 further comprising determining the one or more predicted semantic items associated with the textual input according one or more medical ontologies and/or medical terminology databases.

6. The method of claim 3 wherein processing the medical information to identify one or more semantic items includes processing the textual input to identify words or phrases associated with semantic items.

7. The method of claim 1 further comprising parsing an electronic health record for the patient to identify at least some of the one or more semantic items.

8. The method of claim 1 wherein the presenting of the at least some medical information items of the plurality of medical information items in the second user interface element occurs when a user interacts with the first semantic item.

9. The method of claim 8 wherein presenting the at least some medical information items of the plurality of medical information items in the second user interface element includes causing the second user interface element to be displayed.

10. The method of claim 1 further comprising presenting the one or more semantic items in the first user interface element.

11. The method of claim 10 wherein presenting the semantic items includes color coding the semantic items according to contexts associated with the semantic items.

12. The method of claim 11 wherein each context associated with semantic items is selected from a group including a condition context, a lab result context, a medication context, a symptom context, a procedure context, and a vitals context.

13. The method of claim 1 wherein each semantic item is associated with a context selected from a group including a condition context, a lab result context, a medication context, a symptom context, a procedure context, and a vitals context.

14. The method of claim 1 further comprising populating a third user interface element at least some of the one or more semantic items.

15. The method of claim 1 further comprising detecting that at least some of the medical information associated with a plurality of semantic items and displaying an indicator associated with the at least some medical information in the first user interface element based on the detecting.

16. The method of claim 15 further comprising presenting a menu for disambiguating the medical information by selecting a semantic item from the plurality of semantic items.

17. The method of claim 1 wherein the first user interface element and the second user interface element are displayed simultaneously.

18. The method of claim 1 further comprising identifying at least some semantic items of the one or more semantic items as negated semantic items and presenting a negation indicator along with the identified semantic items.

19. The method of claim 1 wherein the medical information received for the patient is related to a current clinical interaction with the patient and the medical record for the patient includes medical information received in relation to previous clinical interactions with the patient.

20. The method of claim 19 wherein identifying the plurality of medical information items related to the first semantic item includes retrieving clinically pertinent information relevant to the semantic item from the patient's medical record, the clinically pertinent information including one or more of lab values, medications, and test results for the patient.

21. The method of claim 20 wherein presenting the at least some medical information items of the plurality of medical information items in the second user interface includes presenting the clinically pertinent information in conjunction with the first semantic item.

22. The method of claim 1 wherein identifying the plurality of medical information items related to the first semantic item includes retrieving clinically pertinent information relevant to the semantic item from the patient's medical record, the clinically pertinent information including one or more of lab values, medications, and test results for the patient and presenting the at least some medical information items of the plurality of medical information items in the second user interface includes presenting the clinically pertinent information.

23. A system for managing medical information, the comprising:
    a display for displaying a plurality of user interface elements within a graphical user interface;
    an input for receiving medical information for a patient in a first user interface element of the plurality of user interface elements;
    one or more processors configured to:
        process the medical information to identify one or more semantic items, the one or more semantic items including a first semantic item;
        process a medical record for the patient according to the first semantic item, the processing including identifying a plurality of medical information items related to the first semantic item; and
        cause presentation, using the display, of at least some medical information items of the plurality of medical information items in a second user interface element configured to display medical information items related to the first semantic item.

24. Software embodied on a non-transitory, computer readable medium including instructions for implementing a method for managing medical information, the method comprising:
    displaying a plurality of user interface elements within a graphical user interface;
    receiving medical information for a patient in a first user interface element of the plurality of user interface elements;
    processing the medical information to identify one or more semantic items, the one or more semantic items including a first semantic item;
    processing a medical record for the patient according to the first semantic item, the processing including identifying a plurality of medical information items related to the first semantic item; and
    presenting at least some medical information items of the plurality of medical information items in a second user interface element configured to display medical information items related to the first semantic item.

\* \* \* \* \*